United States Patent [19]
Larsen et al.

[11] Patent Number: 6,159,937
[45] Date of Patent: Dec. 12, 2000

[54] IMMUNOMODULATORS

[75] Inventors: Christian Grønhøj Larsen, Aarhus; Borbala Gesser, Hasselager, both of Denmark

[73] Assignee: Steeno Research Group A/S, Odense, Denmark

[21] Appl. No.: 08/765,094

[22] PCT Filed: Jun. 7, 1995

[86] PCT No.: PCT/DK95/00227

§ 371 Date: Jan. 2, 1997

§ 102(e) Date: Jan. 2, 1997

[87] PCT Pub. No.: WO96/01318

PCT Pub. Date: Jan. 18, 1996

[30] Foreign Application Priority Data

Jul. 5, 1994 [DK] Denmark .................. 0800/94

[51] Int. Cl.⁷ .............. A61K 38/08; C07K 7/06; C07H 21/04
[52] U.S. Cl. ................ 514/15; 514/13; 514/14; 530/300; 530/328; 536/23.5
[58] Field of Search ............ 514/14, 15, 13; 530/300, 328; 536/23.5

[56] References Cited

FOREIGN PATENT DOCUMENTS

| 2085291 | 1/1994 | Canada . |
|---|---|---|
| 91/00349 | 1/1991 | WIPO . |
| 93/02693 | 2/1993 | WIPO . |
| 93/17698 | 9/1993 | WIPO . |
| WO94/04180 | 3/1994 | WIPO . |

OTHER PUBLICATIONS

Koonce, et al., Dynein from Dictyostelium: Primary Structure Comparisons Between a Cytoplasmic Motor Enzyme and Flagellar Dynein, The Journal of Cell Biology, vol. 119, No. 6, pp. 1597–1604, Dec. 1992.

*Primary Examiner*—Elizabeth Kemmerer
*Assistant Examiner*—David S. Romeo
*Attorney, Agent, or Firm*—Iver P. Cooper

[57] ABSTRACT

The nonapeptide Ala-Tyr-Met-Thr-Met-Lys-Ile-Arg-Asn (SEQ ID NO:1) and certain related substances are useful as immunomodulators.

44 Claims, 11 Drawing Sheets

FIG. 1

```
                                           19
                                           ↓
mIL10       MPGSALLCCLLLLTGMRISRGQYSREDNNCTHFPVGQSHMLLELRTAF
            |  ||||||||  ||||  |   | ||      |‾|‾|‾||       ||   || ||
hIL10       MHSSALLCCLVLLTGVRASPGQGTQSENSCTHFPGNLPNMLRDLRDAF
              |  |||||    |        |       ||       ‾|  ‾|‾|          ‾||||||||
BCRFI       MERRLVVTLQCLVLL--YLAPECGGTD---QCDNFPQ----MLRDLRDAF
                                                                                |
                                                                               30
SQVKTFFQTKDQLDNILLTDSLMQDFKGYLGCQALSEMIQFYLVEVMPQAEKHGPEIKEHLNSLG
|  ||||||  ||||||  ||   ||  |||||||||||||||||||||| ||||||||   |  ||  | ||||
SRVKTFFQMKDQLDNLLLKESLLEDFKGYLGCQALSEMIQFYLEEVMPQAENQDPDIKAHVNSLG
|||||||||‾||  |||||||||||||||||||‾|||||||‾|||||||||‾||||||||   | ‾||||||
SRVKTFFQTKDEVDNLLLKESLLEDFKGYLGCQALSEMIQFYLEEVMPQAENQDPEAKDHVNSLG
31                                                                             95
                                                       ↓↓
EKLKTLRMRLRRCHRFLPCENKSKAVEQVKSDFNKLQDQGVYKAMNEFDIFINCIEAYMMIKMKS
| ||||||  |||||||||||||‾|‾|‾|||||||||  |||||  | ||||  ||||||| |||||   |
ENLKTLRLRLRRCHRFLPCENKSKAVEQVKNAFNKLQEKGIYKAMSEFDIFINYIEAYMTMKIRN
||||||||||||‾||||||‾|‾|‾|‾|‾|||||||  ||||||||||||||||||‾|||||||||||||||‾| |
ENLKTLRLRLRRCHRFLPCENKSKAVEQIKNAFNKLQEKGIYKAMSEFDIFINYIEAYMTIKAR
96                                                                            160
```

FIG. 2

```
PORCINE IL-10              *       *       *
    PIT          - A - Y - M - T - M - K - M - R - K - N

HUMAN IL-10                *       *       *
    IT 9302      - A - Y - M - T - M - K - I - R - N

BCRFI IL-10                *       *       *
    VIT          - A - Y - M - T - I - K - A - R -
```

Aminoacids marked with * represent key position for receptor binding and are evolutionary well conserved. Compare the IL-10 aminoacid sequence from mouse below.

```
MOUSE IL-10                                *
    MIT          - A - Y - M - M - I - K - M - K - S
```

This sequence is lacking the homology to the important amino acids.

(▲) INDICATES THE LEVEL OF IL-8 WHEN USING rh IL-10 (100 ng/ml).

IMMUNOMODULATORS

FIELD OF INVENTION

The present invention relates to the pharmaceutical use of a substance which is an interleukin 10 (IL-10) agonist, in particular the use of a substance of the invention for the manufacture of a pharmaceutical composition for prevention and/or treatment of diseases, the pathogenesis of which is related to the decreased production and/or function of immunoinhibitory mediators, especially cytokines, and/or is related to an increased production and/or function of certain immuno-inflammatory mediators, especially cytokines. In particular, the invention relates to the use of a substance of the invention for the manufacture of a pharmaceutical composition for prevention and/or treatment of auto-immune diseases (diabetes mellitus, type I; inflammatory diseases of the gastro-intestinal tract; rheumatoid arthritis), arthritis urica (gout), allergy of the skin; allergic reactions in the skin, lungs and respiratory tract (including asthma bronchiale); tissue damage as a result of hypoxia/ischemia (infarction; reperfusion); atherosclerosis; psoriasis; granulomatous disease; chronic myeloid leukaemia; acute myeloid leukaemia; cancer; graft vs. host reaction and conditions related to transplant rejection; fibrosis of the lung; fibrosis of the liver; chronic non-infectious inflammation of the lung; glomerulonephritis; pre-term labour; periodontitis; inflammatory reactions due to virus infections, osteoporosis, septic shock and/or for the manufacture of an anti-conceptive agent.

BACKGROUND OF THE INVENTION

Research from the last two decades has shown that the initiation, regulation and ending of inflammatory reactions as well as the regulation of growth and differentiation within the mammalian organisms is under tight control by a special group of signal polypeptides generally called cytokines. Cytokines are polypeptides which can be produced by most nucleated cells and which transmit regulatory signals between cells, thus forming a communication network between identical or different cell types of the organism. The cytokines are extremely potent mediators and active at concentrations down to $10^{-15}$ M. Cytokines are also key factors for the development of cellular immune reactions, which in turn form the basis for the clinical manifestations of inflammation due to infection, allergy, trauma, graft vs. host reactions and auto-immune diseases. The allergic and auto-immune diseases are explained by abnormalities in the immune system, especially in the T lymphocyte-mediated immunity, but generally these diseases are of unknown etiology. In vitro studies, animal experiments and clinical experimental studies have shown that cytokines play important pathophysiological roles for the inflammatory reactions related to auto-immune diseases, allergy, ischemia, reperfusion injury, trauma, infections, and are important for the development of cancer, atherosclerosis, pregnancy and fetal development, bone homeostasis. Cytokines may be involved in other immunoinflammatory and proliferative diseases as will be described in further detail in the following.

The said diseases are usually chronic and the treatment is palliative, i.e. most of the drugs prescribed in connection with the said diseases are directed at the allaying of symptoms and usually have no curative effect. Other treatments are so-called substitution therapies which involve life-long supplying to the patient of substances, e.g. hormones, needed due to a reduced/insufficient internal production of said substance. Said treatments are often unsatisfactory, imply unwanted and often serious side-effects, and merely delay rather than prevent the progression of the disease. Thus, improved methods of treatments and improved pharmaceutical compositions are highly needed.

Interleukin-10 (IL-10) is a recently described natural endogenous immunosuppressive cytokine, identified in both the murine and human organism. Murine interleukin 10 (mIL-10) was originally described as a cytokine synthesis inhibitory factor released from $TH_2$ helper T-cell clones, but it also carries proliferative effects upon various subsets of lymphocytes, including an enhancing effect upon cloning efficacy of CD4-,8+ murine splenic T cells (4). Human interleukin 10 (hIL-10) has recently been sequenced and revealed to have high homology with mIL-10 at DNA sequence level as well as on amino acid level. Furthermore, swine interleukin 10 has recently been sequenced and revealed to have high homology with human IL-10 at DNA sequence level as well as on amino acid level (88), see also FIG. 2. Also, hIL-10 has high homology with an open reading frame in the Epstein-Barr virus genome, BCRF1, and viral IL-10 does show some activity similar to hIL-10, cf. FIG. 1 (5).

Human IL-10 is produced by activated T cell clones and immortalized B cells, and in addition to its cytokine synthesis inhibitory factor (CSIF) activity, inhibiting the production of several pro-inflammatory cytokines and colony-stimulating factors, it also induces the production of a natural interleukin-1 receptor antagonist protein/peptide (IRAP) by mono-nuclear cells, thereby indirectly inhibiting IL-1 activity. IL-10 also downregulates its own production by monocytes and inhibits the expression of class II MEC expression (12). Further, hIL-10 reduces antigen-specific proliferation of human T cells and $CD4^+$ T cell clones, when using monocytes as antigen-presenting cells. In vivo experiments in mice indicate that the outcome of Leishmania infection is dependent upon the cytokine profile from responding $CD4^+$ T lymphocytes (13). In C57BL/6 mice resistant to Leishmania infection, $CD4^+$ T cells from draining lymph nodes show up-regulation of IFN-γ and IL-2 cytokines, whereas the sensitive BALB/C mice in their draining lymph nodes have $CD4^+$ responding T cells releasing IL-4 and IL-10, which could be demonstrated to correlate with disease progression (13). Thus, IL-10 may exert potent regulatory effects on immunological responses both in vitro and in viva. Further IL-10 strongly affects chemokine biology since human interleukin 10 is a specific chemotactic factor towards CD8+ T cells, while IL-10 suppresses the ability of CD4+, but not CD8+, T cells to migrate in response to the T cell chemotactic cytokine, IL-8 (14). IL-10 also inhibits the chemotactic effect of other chemokines MCP-1/MCAF and RANTES (75). Since IL-10 is a deactivator of monocyte/macrophage functions and an inhibitor of Th1 activity, drugs with full or partial IL-10-like activity may possess therapeutic effect in diseases characterized by imbalance in cytokine production and/or activities.

It has previously been proposed to prepare pharmaceutical compositions comprising hIL-10 or vIL-10, and the use of hIL-10 or vIL-10 for the manufacture of a pharmaceutical composition for the treatment of various conditions such as septic or toxic shock, rheumatoid arthritis, graft-vs-host disease, tissue rejection, diabetes mellitus, autoimmune disorders, leukaemia and cancer has been disclosed in e.g. WO93/02693 and WO94/04180. Moreover, IL-10 antagonists, e.g. antibodies specifically binding to IL-10, have been disclosed in e.g. EP 405 980 and WO94/06473, and it has been contemplated that such antibodies could be useful in the treatment of HIV infected patients.

SUMMARY OF THE INVENTION

According to the present invention, it has been found that a substance other than human interleukin 10 which has one or more of the following properties:

a) induces inhibition of spontaneous IL-8 production by human monocytes, b) induces inhibition of IL-1β induced IL-8 production by human peripheral blood mononuclear cells (PBMC), c) induces production of interleukin-1 receptor antagonistic protein (IRAP) by human monocytes, d) induces chemotactic migration of CD8+ human T lymphocytes in vitro, e) desensitizes human CD8+ T cells resulting in an unresponsiveness towards rhIL-10, f) suppresses the chemotactic response of CD4+ human T lymphocytes towards IL-8, g) suppresses the chemotactic response of human monocytes towards MCAF/MCP-1, h) does not inhibit class II MHC molecule expression on human monocytes, in contrast to human IL-10, i) induces the production of IL-4 by cultured normal human CD4+ T cells, j) reduces the TNFα production in human mixed leukocyte reaction, such as a polypeptide which comprises the amino acid sequence Ala-Tyr-Met-Thr-Met-Lys-Ile-Arg-Asn (SEQ ID NO: 1) or an analogue or variant of said sequence (a nona-peptide with sequence homology to hIL-10, called IT9302), and derivatives thereof can be used for the prevention and/or treatment of certain forms of inflammatory processes, especially forms related to the immune and/or hormone system. It is contemplated (as described in detail in the following description of immunological mechanisms) that the action mechanism is via interference with the action of mediators of the immune system, in particular cytokines such as monokines, lymphokines, chemokines and monokine-receptor antagonists, i.e. that the substance of the invention interferes with/suppresses the production and/or action of certain cytokines and thus inhibits pathological processes leading to tissue damage, and that the substance of the invention induces the production of natural monokine-receptor antagonists thus interfering with/suppressing the action of certain cytokines and thereby inhibiting pathological processes which lead to tissue damage.

An important embodiment of the present invention thus relates to a pharmaceutical composition comprising, as the active ingredient, a substance of the invention. Other embodiments of the invention are a substance which is capable of neutralizing one or more of the activities a) to g) mentioned above, e.g. an antibody, and a pharmaceutical composition comprising such a substance.

In a further aspect, the present invention relates to the use of a substance of the invention for the manufacture of a pharmaceutical composition for substantially inhibiting a biological effect related to a cytokine, i.e. the use of a substance of the invention as an IL-1 receptor antagonist protein/peptide, lymphokine, monokine, interleukin, interferon, chemokine or colony-stimulating factor. Another aspect relates to the use of a substance of the invention for the manufacture of a pharmaceutical composition for the prophylaxis or treatment of a condition related to the disturbance of a cytokine system, i.e. the IL-1 receptor antagonist protein/peptide, lymphokine, monokine, interleukin, interferon, chemokine or colony-stimulating factor system. In another aspect, the invention also relates to a method of treating a condition in a human related to a disturbance in a cytokine system which method comprises administering to the subject an effective amount of a substance of the invention.

The cellular immune system takes part in the development of such disorders as infectious, inflammatory and neoplastic diseases. Immunocompetent cells and their products may play important roles in the initiation, progression and possible chronic nature of development of inflammatory conditions. These disorders are often without known etiology and includes common diseases such as diabetes mellitus, rheumatoid arthritis, inflammatory diseases of the gastrointestinal tract and of the skin. Apart from these examples, cell-mediated immunity or pro-inflammatory mediators, however, contribute to many other inflammatory and proliferative diseases (see Table 2).

TABLE 2

Some diseases where macrophages/T-lymphocyte-mediated immune reactions are considered pathogenetically important Skin diseases:

Psoriasis
Atopic dermatitis
Contact dermatitis
Cutaneous T cell lymphoma (CTCL)
Sezary syndrome
*Pemphigus vulgaris*
*Bullous pemphigoid*
*Erythema nodosum*
Scleroderma
Auto-immune (including rheumatic) diseases:

Uveitis
Bechet's disease
Sarcoidosis Boeck
Sjögren's syndrome
Rheumatoid arthritis
Juvenile arthritis
Reiter's syndrome
Gout
Osteoarthrosis
Systemic lupus erythematosis
Polymyositis
Myocarditis
Primary biliary cirrhosis
Crohn's disease
Ulcerative colitis
Multiple sclerosis and other demyelinating diseases
Aplastic anaemia
Idiopathic thrombocytopenic purpura
Multiple myeloma and B cell lymphoma
Simmons' panhypopituitarism
Graves' disease and Graves' opthalmopathy
Subacute thyreoditis and Hashimoto's disease
Addison's disease
Insulin-dependent diabetes mellitus (type 1)
Other diseases Various clinical syndromes with vasculitis (e.g. polyarteritis nodosa, Wegener's granulomatosis, Giant cell arteritis
Fever, malaise
Anorexia (e.g. in acute and chronic inflammatory and infectious diseases)
Disseminated intravascular coagulation (DIC)
Arteriosclerosis (atherosclerosis)
Shock (e.g. in gram-negative sepsis)
Cachexia (e.g. in cancer, chronic infectious and chronic inflammatory diseases)
Transplant rejection and graft vs. host disease Cytokines T-lymphocytes orchestrate the induction and regulation of cell-mediated immune reactions, and cytokine products (lymphokines) of the T cells initiate and control the immune response (1,2). The lymphocyte-activating mediators (lymphokines) produced by antigen-presenting cells belong to a group of polypeptides called cytokines. Cytokines are transmitters of cell-to-cell communication in both physiological and pathophysiological conditions, and may also function as hormones providing signals between the immune system and other tissues and organs. Cytokines may also be produced by cells outside the immune system and it is generally believed that all nucleated cells are capable of producing one or several cytokines. Thus, e.g. keratinocytes and fibroblasts are potent producers of cytokines and in this system cytokines may function as autocrine or paracrine hormones independent of the immune system (3).

Interleukin-10

Murine interleukin 10 (mIL-10) was originally described as a cytokine synthesis inhibitory factor (CSIF) released from $TH_2$ helper T-cell clones but it has also proliferative effects upon various subsets of lymphocytes, including an enhancing effect upon cloning efficacy of CD4-,8+ murine splenic T cells (4). Human interleukin 10 (hIL-10) has recently been described (5) and has high homology with an open reading frame in the Epstein-Barr virus genome, BCRF1, and viral IL-10 does show some activity similar to hIL-10. In the following, the biochemical, biological, physiological and possible pathophysiological roles of IL-10 will be summarized.

IL-10 Structure

The primary structures of mouse (mIL-10) and human IL-10 (hIL-10) revealed a high degree of nucleotide sequence homology (>80%) throughout their entire length (4, 5). The only significant difference is the insertion of a human Alu repetitive sequence element in the 3'-untranslated region of the hIL-10 cDNA clone. The mIL-10 and hIL-10 cDNAs encode very similar open reading frames (ORF) of 178 amino acids, including hydrophobic leader sequences and corresponding to 73% amino acid homology. mIL-10, which is active on murine cells, does not cross-react significantly on human cells. hIL-10 is an 18 kDa polypeptide which lacks detectable carbohydrate, but mIL-10 is N-glycosylated at a site near its N-terminus which is missing from hIL-10. Both mIL-10 and recombinant hIL-10 (rhIL-10) are expressed as non-covalent homodimers. The extent to which mIL-10 or hIL-10 monomers are biologically active is not yet certain. mIL-10 and hIL-10 with polypeptide "tags" of at least 8 amino acids at the N-terminus and 21 amino acids at the C-terminus showed no detectable loss of activity according to a publication from Moore et al. who were the first to sequence human IL-10 (6). Tagging C and N terminal ends of the whole IL-10 does not necessarily cause functional changes, since tagging is occasional or incidental. The high number of possible amino acid substitutions as described in further detail in the following might also explain while tagging failed to show missing functions. Recombinant mIL-10 and hIL-10 have been expressed in: CDS7 cells, mouse myeloma cells, chinese hamster ovary cells, a baculovirus expression system, and E. coli. The biological activities of these rIL-10 proteins are so far indistinguishable (6).

The mIL-10 gene comprises five exons arrayed over approximately 5.1 kb of DNA. The genomic clone itself encodes an expressible mIL-10 protein. The mIL-10 and hIL-10 genes are on mouse and human chromosome 1 (6, 7).

mIL-10 and hIL-10 exhibit strong DNA and amino acid sequence homology to an open reading frame in the Epstein-Barr virus genome, BCRF1, and the homology is confined to the mature protein coding sequence and is not detected in the signal sequence or 5'- and 3'-untranslated sequences (5). Of the three sequences, mIL-10 and hIL-10 are the more closely related pair at the DNA sequence level (81%), while the DNA sequences encoding the mature hIL-10 and BCRF1 proteins have 71% homology. The homology between hIL-10 and BCRF1 is 84% on the amino acid level. It is hypothesized that the mIL-10 and hIL-10 genes are evolved from a common ancestor, while BCRF1 represents an ancestral processed, captured cellular cytokine gene and that the BCFR1 protein has been constrained to resemble hIL-10. BCFR1 is expressed during the lytic cycle of the EBV. The BCFR1 ORF encodes a 17 kDa secreted polypeptide which, like hIL-10, contains little or no glycosylation. BCFR1 displays some activities of IL-10 and has been called viral IL-10 (vIL-10), although its activity has been found to be 10% of hIL-10.

IL-10 Activity on Cytokine Production hIL-10 inhibits the production of a number of cytokines including interferon-γ (IFN-γ), Tumor Necrosis Factor-α (TNF-α), Granulocyte Macrophage Colony Stimulating Factor (GM-CSF), Granulocyte-CSF (G-CSF), IL-1α, IL-1β, IL-2, IL-6, IL-8 and Monocyte Chemotactic polypeptide-1 (MCP-1/MCAF) by monocytes/macrophages and/or T lymphocytes (4, 5). IL-10 also inhibits the ability of monocytes to migrate as a response to the chemokine MCP-1/MCAF (75). Further, hIL-10 induces the production of an endogenous, natural interleukin-1 receptor antagonist (IRAP) (6), which inhibits IL-1α and IL-1β by competing with receptor binding. Since IL-8 is strongly inducible by IL-1α and by IL-1β, IL-10 exerts part of its inhibitory effect on IL-8 production by stimulating the production of the IL-1-receptor antagonist IRAP. This last mechanism is of considerable importance for the present invention as described and exemplified in the following. IRAP has anti-inflammatory activities (9), and its therapeutic effect in rheumatoid arthritis has been suggested (10). Also, IRAP proved to be effective in the treatment of sepsis syndrome and a dose-dependent, 28-day survival benefit was associated with IRAP treatment (p=0.015) in a study by Fisher et al. (11). IRAP may exert parts of its anti-inflammatory effects by inhibiting chemokine-production such as the production of IL-8.

IL-10 and Antigen Expression

IL-10 inhibits the expression of class II MHC expression on human monocytes (8). Constitutive and IL-4 or IFN-γ induced expression of HLA-DR/DP and DQ was inhibited by hIL-10 (12). In addition, monocytes pre-incubated with IL-10 are refractory to subsequent induction of class II MHC expression by IL-4 or IFN-γ. IL-10 inhibits class II expression by human monocytes following activation by LPS (12, 76). BALB/c mice given 1 to 10 mg of IL-10 concomitantly with a lethal dose of LPS were protected from death (6).

IL-10 inhibits nitrogen intermediates and superoxide anions. IL-10 also inhibits reactive nitrogen intermediate (NO) as well as reactive oxygen intermediates ($H_2O_2$) by macrophages following activation by IFN-γ (13).

IL-10 and T Cell Activity

IL-10 has also modulatory effects on T cell functions/activity. Thus, hIL-10 is a potent chemotactic factor to CD8+ T lymphocytes, while hIL-10 does not show chemotaxis towards CD4+ T cells (14). Additionally, IL-10 suppresses the capacity of CD4+ T cells to respond to the chemotactic signals of the β-chemokine RANTES as well as the α-chemokine IL-8. hIL-10 also directly inhibits the proliferation of human peripheral blood T cells and CD4+ T cell clones (14).

IL-10 and B Lymphocytes hIL-10 co-stimulates B-lymphocyte proliferation induced by cross-linking surface Ig with immobilized anti-IgM antibody, and this effect is enhanced when B-cells are stimulated by cross-linking of their CD40 antigen with anti-CD40 antibody and mouse L cells expressing human FcγRII/CD32 (15). The effect of IL-10 on proliferation and differentiation of activated human B cells suggests that this cytokine may account for much of the superior ability of T cells expressing hIL-10 to provide help for B cell responses.

IL-10 as a Homeostatic Factor for the Immune System

The physiological consequences of the functions of IL-10, mentioned above, are believed to be a certain degree of homeostasis on the immune system. Thus, IL-10 clearly inhibits helper T cells functions and probably stimulates T cells with suppressor functions. Therefore, like IL-4, IL-10 is believed to regulate the balance between Th1 and Th2 cytokine profiles of T cells. Especially, it is believed that IL-10 inhibits the differentiation of Thl cells. Since Thl cells are characterized by the production of cytokines (IFN-γ and IL-2) which favour cell-mediated immune responses while Th2 cells produce cytokines (IL-4, IL-5 and IL-10) which favour a humoral response and suppress a cell-mediated immune response, IL-10 is likely to suppress a T cell-mediated immune reaction such as delayed type hypersensitivity reactions, while it favours humoral responses.

As a consequence of the features of IL-10 mentioned above, the activity of IL-10 has been described as an inhibitor of macrophage and Thl cytokine synthesis. Therefore it has been studied whether lack of IL-10 production and/or activity may play a role in diseases where an enhanced cell-mediated immunoreactivity is believed to play a role for the disease, such as in auto-immune diseases and inflammation. Anti-IL-10 antibody-treated mice show a stronger inflammatory response to monokine-induced inflammation and are significantly more susceptible to death induced by LPS-induced septic shock, a monokine-mediated inflammatory reaction (16). Also, IL-10 knock-out mice spontaneously develop inflammatory reactions of the gut similar to that of colitis ulcerosa (17). Additionally, it has been investigated whether IL-10 plays a role in different parasite, mycobacterial or viral infections, and IL-10 has been shown to play a pathophysiological role in the immune-paresis related to the infection with *Schistosoma mansoni* (18). Also a role in *Mycobacterium leprae* infections has been suggested. Recently, it has been found that AIDS patients with a poor prognosis have a higher level of IL-10 in plasma, and it has been suggested that this contributes to the immune paresis which is known from AIDS (19).

Therapeutic Considerations

These in vivo results/data strongly suggest a homeostatic role of IL-10 in controlling cell-mediated and monokine-amplified immune inflammation and indicate the wide-ranged therapeutical applications of IL-10 or a drug with IL-10-like activity in the treatment of diseases which are characterized by a decreased/insufficient production and/or activity of IL-10. Since the substance of the present invention exemplified by IT9302 exerts IL-10-like activity by 1) inducing IRAP production by human monocytes,
2) inhibiting spontaneous IL-8 production by human monocytes,
3) inhibiting IL-1β-stimulated IL-8 production by peripheral blood mononuclear cells (PBMC),
4) stimulating chemotactic migration of CD8+, but not CD4+, human T lymphocytes,
5) desensitizing human CD8+ T cells towards rhIL-10-induced chemotactic migration,
6) inhibiting IL-8-mediated human CD4+ T cell chemotaxis, and
7) inhibiting MCP-1/MCAF-mediated human monocyte chemotaxis,
8) inducing the production of IL-4 by cultured normal human CD4+ T cells,
9) reducing the TNFA production in human mixed leucocyte reaction, this polypeptide and analogues thereof may thus possess the same therapeutic possibilities as hIL-10. Table 3 lists some diseases where an immune-modulator like IL-10 or an immune-modulator with IL-10-like activity may have therapeutic importance:

TABLE 3

Some diseases where an immune-modulator with IL-10-like activity, due to its induction of IRAP production and/or inhibition of cytokine-production and/or activity may have therapeutic importance (ref. 20–74)

Pre-term labour caused by infection or other conditions
Rheumatoid arthritis
Lyme's arthritis
Gout
Sepsis syndrome
Hyperthermia
Ulcerative colitis or enterocolitis
Osteoporosis
Cytomegalovirus
Periodontal diseases
Glomerulonephritis
Chronic, non-infectious inflammation of the lung (e.g. sarcoidosis and smoker's lung)
Granuloma formation
Fibrosis of the liver
Fibrosis of the lung
Transplant rejection
Graft vs. host disease
Chronic myeloid leukaemia
Acute myeloid leukaemia
Other neoplastic diseases
Asthma bronchiale
Diabetes mellitus, type I (insulin dependent)
Arteriosclerosis/atherosclerosis
Psoriasis
Chronic B lymphocyte leukaemia
Common variable immunodeficiency
Side-effects using other biological response modifiers
Disseminated intravascular coagulation
Systemic sclerosis
Encephalomyelitis
Lung inflammation
Hyper IgE syndrome
Enterocolitis
Cancer metastasis and growth
Adoptive immune therapy
Acquired respiratory distress syndrome
Sepsis
Reperfusion syndrome
Postsurgical inflammation
Organ transplantation
Alopecia

DETAILED DESCRIPTION OF THE INVENTION

Development of an IL-10-Homologous Nonapeptide With IL-10- Like Activity

Partial sequences of hIL-10 having a length of 9 amino acids was chosen according to the principle that the sequences should possess high homology between vIL-10 and hIL-10, but as low homology to mIL-10 as possible. This strategy was based on the fact that vIL-10 cross-reacts partly with hIL-10, while mIL-10 does not cross-react with hIL-10 (see above). Thus, sequences of the hIL-10 responsible for certain activities in the human organism may be located at domains where there is high homology between hIL-10 and vIL-10 but low in relation to mIL-10.

The signal polypeptide of hIL-10 is supposed to consist of the first 18 amino acids. The mature protein starts from amino acid No. 19 (No. 1 in the functional protein, which is a serine), and the total protein is containing 160 amino acids. By looking at the human and viral IL-10 COOH-terminal sequences and in particular position 157 and 159, containing lysine and arginine residues, this domain was found to be favourable for being partly responsible for receptor binding. (FIGS. 1 and 2).

After screening several candidates, obtained by chemical synthesis, for IL-10-like activity, it was found that a synthetic nonapeptide, IT9302, possessed some immunosuppressive activities which mimic those of hIL-10 as described in further detail in the following examples. IT9302 corresponds to a nonapeptide sequence from the C-terminal end of hIL-10 with the following amino acid sequence:

$NH_2$-Ala-Tyr-Met-Thr-Met-Lys-Ile-Arg-Asn-COOH (SEQ ID NO:1)

IT9302 has 100% homology with a segment of hIL-10 corresponding to amino acids Nos. 152 to 160 at the C-terminal end. Furthermore, this polypeptide sequence has 6 amino acids in common with the virus vIL-10 in the corresponding area, see FIGS. 1 and 2, which means that 6 of 9 or 66% of the amino acids are homologous as defined herein, and 4 amino acids in common with mIL-10, i.e. 4 of 9 or 44%. This nonapeptide is the only sequence obtained or derived from hIL-10 and examined until now which has the special properties demonstrated in the examples. Until contemplated by the present inventors, no one has pointed to this sequence as a functional domain.

In its broadest aspect, the present invention thus relates to a substance which exhibits hIL-10 agonist activity, i.e. a substance other than human interleukin 10 which has one or more of the following properties:

a) induces inhibition of spontaneous IL-8 production by human monocytes, b) induces inhibition of IL-1γ induced IL-8 production by human peripheral blood mononuclear cells (PBMC), c) induces production of interleukin-1 receptor antagonistic protein (IRAP) by human monocytes, d) induces chemotactic migration of CD8+ human T lymphocytes in vitro, e) desensitizes human CD8+ T cells resulting in an unresponsiveness sponsiveness towards rhIL-10, f) suppresses the chemotactic response of CD4+ human T lymphocytes towards IL-8, g) suppresses the chemotactic response of human monocytes towards MCAF/MCP-1, h) does not inhibit class II MHC molecule expression on human monocytes, in contrast to human IL-10, i) induces the production of IL-4 by cultured normal human CD4+ T cells, j) reduces the TNFα production in human mixed leukocyte reaction.

Among these activities, d) to g) are considered the most unique. One important embodiment of the invention is a substance which exhibits hIL-10 agonist activity as defined above and which comprises the amino acid sequence Ala-Tyr-Met-Thr-Met-Lys-Ile-Arg-Asn (SEQ ID NO: 1) or an analogue or variant of said sequence. This sequence, and all other polypeptide sequences in the present specification and claims, are, also when not explicitly stated, written from the N-terminal to the C-terminal end in the conventional format.

The nonapeptide IT9302 is very potent to induce different functions and is very stable, and it is presumed that it cannot be incorrectly coupled to receptors. A nonapeptide has been chosen because generally a 9 amino acid polypeptide sequence unique for a protein. However, it is to be noted that the 6 amino acids at the very end of hIL-10 seem to be the most important ones. Within the scope of the present invention is thus a substance or polypeptide comprising a subsequence of the amino acid sequence Ala-Tyr-Met-Thr-Met-Lysile-Arg-Asn (SEQ ID NO:1).

It is considered likely that some amino acid substitutions will not have adverse effects on the hIL-10 agonist activity as defined herein as long as the threonine, the lysine and the arginine are present and with one amino acid placed inbetween.

In one aspect, the present invention thus relates to a polypeptide having the formula Thr-$X_4$-Lys-$X_5$-Arg-$X_6$ (SEQ ID NO:19), wherein $X_4$ and $X_5$ are independently selected from the group consisting of Met, Ile, Leu and Val; and $X_6$ is selected from the group consisting of Asn, Asp, Gln and Glu, with the proviso that the polypeptide is not Thr-Met-Lys-Ile-Arg-Asn.

In another aspect, the invention relates to a polypeptide having the formula $X_3$-Thr-$X_4$-Lys-$X_5$-Arg-$X_6$ (SEQ ID NO:20), wherein $X_3$, $X_4$ and $X_5$ are independently selected from the group consiting of Met, Ile, Leu and Val; and $X_6$ is selected from the group consisting of Asn, Asp, Gln and Glu.

In yet a further aspect, the invention relates to polypeptides having the formula $X_2$-$X_3$-Thr-$X_4$-Lys-$X_5$-Arg-$X_6$ (SEQ ID NO:21), wherein $X_2$ is Tyr or Phe, $X_3$, $X_4$ and $X_5$ are independently selected from the group consisting of Met, Ile, Leu and Val; and $X_6$ is selected from the group consisting of Asn, Asp, Gln and Glu.

Preferred embodiments of the invention are polypeptides having the formula $X_1$-$X_2$-$X_3$-Thr-$X_4$-Lys-$X_5$-Arg-$X_6$ (SEQ ID NO:22), wherein $X_1$ is Ala or Gly, $X_2$ is Tyr or Phe, $X_3$, $X_4$ and $X_5$ are independently selected from the group consisting of Met, Ile, Leu and Val; and $X_6$ is selected from the group consisting of Asn, Asp, Gln and Glu.

The present invention thus relates to a substance or polypeptide which comprises an amino acid sequence as defined above, with the proviso that the substance or polypeptide is not human IL-10.

Examples of specific polypeptides which are presumed to have hIL-10 agonist activity as defined above are as follows:

1. $NH_2$-Ala-Tyr-Met-Thr-<u>Ile</u>-Lys-<u>Met</u>-Arg-Asn-COOH (SEQ ID NO:2)
2. $NH_2$-Ala-<u>Phe</u>-Met-Thr-<u>Leu</u>-Lys-<u>Leu</u>-Arg-Asn-COOH (SEQ ID NO:3)
3. $NH_2$-Ala-Tyr-Met-Thr-Met-Lys-<u>Val</u>-Arg-<u>Glu</u>-COOH (SEQ ID NO:4)
4. $NH_2$-Gly-Tyr-Met-Thr-Met-Lys-Ile-Arg-Asp-COOH (SEQ ID NO:5)
5. $NH_2$-Ala-Phe-Met-Thr-Met-Lys-Ile-Arg-Asp-COOH (SEQ ID NO:6)

6. NH$_2$-Ala-Tyr-Ile-Thr-Met-Lys-Ile-Arg-Asp-COOH (SEQ ID NO:7)
7. NH$_2$-Ala-Tyr-Leu-Thr-Met-Lys-Ile-Arg-Asp-COOH (SEQ ID NO:8)
8. NH$_2$-Ala-Tyr-Val-Thr-Met-Lys-Ile-Arg-Asp-COOH (SEQ ID NO:9)
9. NH$_2$-Ala-Tyr-Met-Thr-Ile-Lys-Ile-Arg-Asp-COOH (SEQ ID NO:10)
10. NH$_2$-Ala-Tyr-Met-Thr-Leu-Lys-Ile-Arg-Asp-COOH (SEQ ID NO:11)
11. NH$_2$-Ala-Tyr-Met-Thr-Val-Lys-Ile-Arg-Asp-COOH (SEQ ID NO:12)
12. NH$_2$-Ala-Tyr-Met-Thr-Met-Lys-Ile-Arg-Asp-COOH (SEQ ID NO:13)
13. NH$_2$-Ala-Tyr-Met-Thr-Met-Lys-Met-Arg-Asp-COOH (SEQ ID NO:14)
14. NH$_2$-Ala-Tyr-Met-Thr-Met-Lys-Val-Arg-Asp-COOH (SEQ ID NO:15)
15. NH$_2$-Ala-Tyr-Met-Thr-Met-Lys-Ile-Arg-Gln-COOH (SEQ ID NO:16)
16. NH$_2$-Ala-Tyr-Met-Thr-Met-Lys-Ile-Arg-Glu-COOH (SEQ ID NO:17)

For comparison, another nonapeptide called IT9301 with 100% homology to a sequence of hIL-10 was synthesized. This polypeptide, IT9301, corresponds to a nonapeptide sequence starting at the N-terminal end of hIL-10, (amino acids nos. 19 to 27, i.e. the first 9 amino acids of the mature protein) and has the following amino acid sequence:

NH$_2$-Ser-Pro-Gly-Gln-Gly-Thr-Gln-Ser-Glu-COOH  (SEQ ID NO:18)

This polypeptide showed no IL-10-like activity using the techniques described below and was only chosen because it is at the other end of hIL-10 and mostly served as a control for negative results. It does not have the characteristics of the C-terminal sequence with regard to sequence homology to vIL-10, and favourable amino acids for receptor binding. IT9301 was tested in the IL-1β induced peripheral blood mononuclear cell system for IL-8 production, but did not induce any inhibition at all of the IL-8 production from the cells.

In accordance with the present invention, the term "a hIL-10 agonist substance of the invention" comprises any pharmaceutically active and acceptable compound being identical or structurally similar to IT9302 and exhibiting relevant biological actions similar to those of IT9302, including derivatives of IT9302, especially pharmaceutically acceptable salts, esters and solvates as well as conjugates of IT9302 or of the IT9302 derivatives including peptido-mimetics. Covalent coupling of IT9302 at the NH$_2$-terminal end to appropriate carriers, e.g. polyethylene glycol or sugar might extend the half-life of the polypeptide in vivo.

The following definitions are employed in the present text:

"Cytokine" is a general term for a proteinaceous mediator released primarily but not exclusively by a cell population of the immune system as a response to a specific stimulating agent, e.g. a specific antigen or an alloantigen; or a non-specific, polyclonal activator, e.g. an endotoxin or other cell wall components of a gram-negative bacterium.

"Lymphokine" is a general term for a proteinaceous mediator released by sensitized lymphocytes as a response to a stimulating agent, e.g. a specific antigen or an alloantigen; or by a lymphocyte challenged by a polyclonal activator, e.g. an endotoxin or other cell wall components of a gram-negative bacterium.

"Interleukin" is a general term for a proteinaceous mediator released primarily but not exclusively by a macrophage, T, B, or NK cell as a response to a stimulating agent, e.g. a specific antigen or an alloantigen; or by a lymphocyte challenged by a polyclonal activator, e.g. an endotoxin or other cell wall components of a gram-negative bacterium.

"Monokine" is a general term for a proteinaceous mediator released primarily but not exclusively by a mononuclear phagocyte (e.g. a monocyte or a macrophage or a Kupffer cell (liver) or a Langerhans' cell (skin) as a response to any stimulating agent.

"Chemokine" is a general term for a proteinaceous chemotactic and/or leukocyte-activating mediator released primarily but not exclusively by a cell population of the immune system as a response to a specific stimulating agent, e.g. a specific antigen or an alloantigen; or a non-specific, polyclonal activator, e.g. an endotoxin or other cell wall components of a gram-negative bacterium and belonging to a particular gene family either the chemokine-α gene family or the chemokine-β gene family.

"Interferon" is a general term for a proteinaceous antiviral and/or monocyte-activating mediator released primarily but not exclusively by a cell population of the immune system as a response to a virus or an interferon inducer such as a polynucleotide; in particular cells of the immune system as a response to a specific stimulating agent, e.g. a specific antigen or an alloantigen; or a non-specific, polyclonal activator, e.g. an endotoxin or other cell wall components of a gram-negative bacterium.

"Colony-stimulating factor" is a general term for a proteinaceous, haematopoietic colony-stimulating mediator released primarily but not exclusively by a cell population of the immune system as a response to a specific stimulating agent, e.g. a specific antigen or an alloantigen; or a non-specific, polyclonal activator, e.g. an endotoxin or other cell wall components of a gram-negative bacterium.

"Polypeptide" as used herein means both short peptides with a length of at least two amino acid residues and at most 10 amino acid residues, oligopeptides (11–100 amino acid residues), and longer peptides (the usual interpretation of "polypeptide", i.e. more than 100 amino acid residues in length) as well as proteins (the functional entity comprising at least one peptide, oligopeptide, or polypeptide which may be chemically modified by being glycosylated, by being lipidated, or by comprising prosthetic groups). The definition of polypeptides also comprises native forms of peptides/proteins in humans as well as recombinant proteins or peptides in any type of expression vectors transforming any kind of host, and also chemically synthesized peptides.

One embodiment of the present invention relates to a polypeptide comprising a subsequence of the sequence of human IL-10 and which has a degree of homology to vIL-10 which is 66% and a degree of homology to mIL-10 which is 44%, in particular SEQ ID NO:1. By the term "homology" is meant the identity in sequences of amino acids in segments of two or more amino acids when matched with respect to identity and position of the amino acids of the polypeptides.

Homology as the term is used herein is thus a measure of similarity between two amino acid (or nucleotide) sequences. Homology is expressed as the fraction or percentage of matching amino acids (or bases) after two sequences (possibly of unequal length) have been aligned. The term alignment is used in the sense defined in (76). Roughly, two sequences are aligned by maximizing the number of matching bases (or amino acids) between the two sequences with the insertion of a minimal number of "blank" or "null" bases into either sequence to bring about the maximum overlap.

The term "homologous" is thus used here inter alia to illustrate the degree of identity between the amino acid sequence of a given polypeptide and the amino acid sequence of IT9302. The amino acid sequence to be compared with the amino acid sequence of IT9302 may be deduced from a nucleotide sequence such as a DNA or RNA sequence, e.g. obtained by hybridization as defined in the following, or may be obtained by conventional amino acid sequencing methods. The degree of homology is preferably determined on the amino acid sequence of a mature polypeptide, i.e. without taking any leader sequence into consideration. Generally, only coding regions are used when comparing nucleotide sequences in order to determine their internal homology.

Although it is contemplated that a substantial degree of homology to hIL-10 and vIL-10 is beneficial, it is not unlikely that subsequences of the subsequence of hIL-10 which show a lower degree of homology to vIL-10, say, e.g., 50%, 55% or 60% , may also show one or more beneficial hIL-10 agonist activities. Moreover, as discussed above, it is not deemed absolutely necessary that the degree of homology to hIL-10 is 100%. Within the scope of the present invention are also polypeptides having a lower degree of homology to hIL-10, such as 75%, 80%, 85%, 90% or 95%, although 100% is preferred.

Such polypeptides may be considered analogues of the nonapeptide. By the term "an analogue or variant thereof" is thus meant a polypeptide not having exactly the amino acid sequence Ala-Tyr-Met-Thr-Met-Lys-Ile-Arg-Asn (SEQ ID NO:1), but still having "hIL-10 agonist activity" as defined above. Generally, such polypeptides will be polypeptides which vary e.g. to a certain extent in the amino acid composition, or the post-translational modifications e.g. glycosylation or phosphorylation, as compared to IT9302 described in the examples.

The term "analogue" or "variant" is thus used in the present context to indicate a protein or polypeptide having a somewhat different, but still similar, amino acid sequence to the amino acid sequence of IT9302, allowing for minor variations that alter the amino acid sequence, e.g. deletions, site directed mutations, insertions of extra amino acids, or combinations thereof, to generate polypeptide analogues of IT9302.

Site-directed mutagenesis provides one convenient way to effect conservative amino acid substitutions, and the like, in the native protein sequence. Alternatively, analogues may be prepared by the well known methods of liquid or solid phase polypeptide synthesis utilizing the successive coupling of the individual amino acids of the polypeptide sequence, or the polypeptide can be synthesized by the coupling of individual amino acids forming fragments of the polypeptide sequence which are later coupled so as to result in the desired polypeptide.

"Conservative" as used herein means (i) that the alterations are as conformationally neutral as possible, that is, designed to produce minimal changes in the tertiary structure of the mutant polypeptides as compared to the native protein, and (ii) that the alterations are as antigenically neutral as possible, that is designed to produce minimal changes in the antigenic determinants of the mutant polypeptides as compared to the native protein. Conformational neutrality is desirable for preserving biological activity, and antigenic neutrality is desirable for avoiding the triggering of immunogenic responses in patients or animals treated with the substances of the invention. Although it is difficult to select with absolute certainty which alternatives will be conformationally and antigenically neutral, rules exist which can guide those skilled in the art to make alterations that have high probabilities of being conformationally and antigenically neutral, see e.g. (77) and (78). Some of the more important rules include (1) replacement of hydrophobic residues is less likely to produce changes in antigenicity because they are likely to be located in the protein's interior, e.g. Berzofsky (cited above) and Bowie et al. (cited above); (2) replacement of physicochemically similar, i.e. synonymous, residues is less likely to produce conformational changes because the replacing amino acid can play the same structural role as the replaced amino acid; and (3) alteration of evolutionarily conserved sequences is likely to produce deleterious conformational effects because evolutionary conservation suggests sequences may be functionally important. In addition to such basic rules for selecting mutein sequences, assays are available to confirm the biological activity and conformation of the engineered molecules. Biological assays for the substances of the invention are described more fully in the examples. Changes in conformation can be tested by at least two well known assays: the microcomplement fixation method, e.g. (79) and (80) used widely in evolutionary studies of the tertiary structures of proteins; and affinities to sets of conformation-specific monoclonal antibodies, e.g. (81).

An important embodiment of the present invention thus relates to a polypeptide in which at least one amino acid residue has been substituted with a different amino acid residue and/or in which at least one amino acid residue has been deleted or added so as to result in a polypeptide comprising an amino acid sequence being different from the amino acid sequence or a subsequence of said amino acid sequence as defined in the following, but essentially having hIL-10 agonist activity as defined above.

An interesting embodiment of the invention relates to a polypeptide which is an analogue and/or comprises at least part of the polypeptide of the invention amounting in total from 10 to 100 amino acids, e.g. at least 12 amino acids, at least 15 amino acids, at least 20 amino acids or at least 30 amino acids.

In a preferred embodiment of the invention, the substance or polypeptide is used in substantially pure form. To obtain this, purification of the polypeptide may be required. Examples of the procedures employed for the purification of polypeptides are: (i) immunoprecipitation or affinity chromatography with antibodies, (ii) affinity chromatography with a suitable ligand, (iii) other chromatography procedures such as gel filtration, ion exchange or high performance liquid chromatography or derivatives of any of the above, (iv) electrophoretic procedures like polyacrylamide gel electrophoresis, denaturating polyacrylamide gel electrophoresis, agarose gel electrophoresis and isoelectric focusing, (v) any other specific solubilization and/or purification techniques.

Within the scope of the present invention is also a nucleotide sequence encoding a polypeptide as defined above, in particular a nucleotide sequence encoding a polypeptide comprising or being the amino acid sequence SEQ ID NO:1, e.g. a nucleotide sequence comprising the sequence GCC TAC ATG ACA ATG AAG ATA CGA AAC (SEQ ID NO:23) or a nucleotide sequence encoding a polypeptide having a subsequence of said amino acid sequence. Moreover, a modified nucleotide sequence which differs from the nucleotide sequence above in that at least one nucleotide has been deleted, substituted or modified or at least one additional nucleotide has been inserted so as to result in a nucleotide sequence which encodes a polypeptide having hIL-10 agonist activity is within the scope of the invention.

In the present specification and claims, the term "subsequence" designates a sequence which preferably has a size of at least 18 nucleotides, more preferably at least 21 nucleotides, and most preferably at least 24 nucleotides. In a number of embodiments of the invention, the subsequence or analogue of the nucleotide sequence of the invention will comprise at least 27 nucleotides, such as at least 30 nucleotides or at least 45 nucleotides. The polypeptide encoded by the "subsequence" should conform to at least one of the criteria a)–g) above and/or the nucleotide "subsequence" should hybridize with the nucleotide sequence comprising the sequence SEQ ID NO:23 under high stringency conditions.

The term "highly stringent" when used in conjunction with hybridization conditions is as defined in the art that is 5–10° C. under the melting point $T_m$, cf. Sambrook et al, 1989, pages 11.45–11.49.

The term "analogue" with regard to the DNA fragments of the invention includes a nucleotide sequence which encodes a polypeptide identical or substantially identical to the polypeptide encoded by the DNA referred to above. It is well known that the same amino acid may be encoded by various codons, the codon usage being related, inter alia, to the preference of the organisms in question expressing the nucleotide sequence. Thus, one or more nucleotides or codons of the DNA fragment of the invention may be exchanged by others which, when expressed, result in a polypeptide identical or substantially identical to the polypeptide encoded by the DNA fragment shown above.

Furthermore, the terms "analogue", and "subsequence" are intended to allow for variations in the sequence such as substitution, insertion (including introns), addition and rearrangement of one or more nucleotides, which variations do not have any substantial adverse effect on the hIL-10 agonist activity of the polypeptide encoded by the DNA fragment or a subsequence thereof. The invention thus also includes a nucleotide sequence encoding a polypeptide having a subsequence of the amino acid sequence SEQ ID NO:1.

The polypeptides of the invention can be produced using recombinant DNA technology. An important embodiment of the present invention relates to an expression system comprising a nucleotide sequence of the invention. Within the scope of the invention is thus also an expression system comprising a nucleotide sequence of the invention, such as a replicable expression vector which carries and is capable of mediating the expression of a nucleotide sequence as defined above. The organism which is used for the production of the polypeptide tide of the invention may be a higher organism, e.g. an animal, or a lower organism, e.g. a microorganism such as *Escherichia coli*, a yeast, a protozoan, or cell derived from a multicellular organism such as a fungus, an insect cell, a plant cell, a mammalian cell or a cell line, which carries an expression system as defined above.

Irrespective of the type of organism used, the DNA fragment of the invention is introduced into the organism either directly or by means of a suitable vector. Alternatively, the polypeptides may be produced in the mammalian cell lines by introducing the DNA fragment or an analogue or a subsequence thereof of the invention either directly or by means of an expression vector. The polypeptides of the invention may also be produced by chemical synthesis as discussed above.

The invention furthermore relates to a plasmid vector containing a DNA sequence coding for a polypeptide of the invention or a fusion polypeptide as defined herein. In one particular important embodiment, the DNA fragment or an analogue or subsequence thereof of the invention or a fusion DNA fragment of the invention as defined herein may be carried by a replicable expression vector which is capable of replicating in a host organism or a cell line.

The vector may in particular be a plasmid, phage, cosmid, mini-chromosome or virus. In an interesting embodiment of the invention, the vector may be a vector which, when introduced in a host cell, is integrated in the host cell genome.

The polypeptide produced as described above may be subjected to post-translational or post-synthetic modifications as a result of thermal treatment, chemical treatment (formaldehyde, glutaraldehyde etc.) or enzyme treatment (peptidases, proteinases and protein modification enzymes). The polypeptide may be processed in a different way when produced in an organism as compared to its natural production environment. As an example, glycosylation is often achieved when the polypeptide is expressed by a cell of a higher organism such as yeast or preferably a mammal. Glycosylation is normally found in connection with amino acid residues Asn, Ser, Thr or hydroxylysine.

One embodiment of the invention thus relates to a method of producing a polypeptide as defined above comprising the following steps of:

(a) inserting a nucleotide sequence as defined above in an expression vector, (b) transforming a suitable host organism with the vector produced in step (a), (c) culturing the host organism produced in step (b) under suitable conditions for expressing the polypeptide, (d) harvesting the polypeptide, and (e) optionally subjecting the polypeptide to post-translational modification.

It is contemplated that antagonists effect to hIL-10 or vIL-10 can be achieved inter alia by using antibodies binding specifically to the nonapeptide IT9302, and that these can be used in therapy for neutralizing high concentration of IL-10.

In another aspect, the present invention thus relates to an antibody which specifically binds to the polypeptide of the invention.

The term "antibody" refers to a substance which is produced by a mammal or more precisely a cell of mammalian origin belonging to the immune system as a response to exposure to a polypeptide antigen of the invention. In the present specification and claims "an antibody" is defined as consisting essentially of the specifically binding basic unit which consists of two heavy chains and two light chains. In its broadest aspect, however, the concept of an antibody should also include e.g. a dimer or pentamer of the basic unit.

The variant domain of an antibody is composed of variable and constant sequences. The variant part of the domain is called the idiotype of the antibody. This part of the antibody is responsible for the interaction with the antigen, the antigen binding. In the present context, the term antibody is understood as the whole antibody molecule or any fragments thereof. An antibody can be fragmented during and/or after the production. It can also be made in the fragmented form to begin with and used as such or used after joining different fragments. Especially interesting fragments are binding fragments of the antibodies of the invention, e.g. Fab or Fab' fragments.

The idiotypic (antigen binding) structure of the antibody is antigenic and can thus give rise to specific antibodies directed against the idiotypic structure. The antibodies raised against the idiotype are called the anti-idiotypic antibodies. Such antibodies may mimic the structure of the original antigen and therefore may function as the original antigen. Such antibodies may be able to substitute the original antigen for a part or all of the functions, usability and properties of the original polypeptide of the invention.

The antibodies of the invention comprise polyclonal antibodies as well as monoclonal antibodies.

The antibody or fragments thereof may be of a monospecific (polyclonal) kind. The monospecific antibody may be prepared by injecting a suitable animal with a substantially pure preparation of the polypeptide of the invention. This can be followed by one or more booster injections at suitable intervals before the first bleeding. The animals are bled about 5–7 days after each immunization. Antibodies may optionally be isolated from the serum using standard antibody purification techniques.

The animal used for the preparation of antibodies binding to the polypeptide of the invention is preferably selected from the group consisting of rabbit, monkey, sheep, goat, mouse, rat, pig, horse and guinea pigs. The cells producing the antibodies may be spleen cells or peripheral blood lymphocytes.

A monoclonal antibody or fragments thereof may be raised against an essential component of the polypeptide, i.e. an epitope. The monoclonal antibody may be produced using conventional techniques (Köhler and Milstein, 1975) by use of a hybridoma cell line, or by clones or subclones thereof or by cells carrying genetic information from the hybridoma cell line producing said monoclonal antibody. The monoclonal antibody may be produced by fusing cells producing said monoclonal antibody with cells of a suitable cell line, and cloning the resulting hybridoma cells producing said monoclonal antibody. body. Alternatively, the monoclonal antibody may be produced by immortalizing an unfused cell line producing said monoclonal antibody. The monoclonal antibodies are ultimately harvested from the cell growth medium. Hybridoma cells used to make monoclonal antibody may be grown in vitro or in the body cavity of an animal. The monoclonal antibody or fragments thereof may also be made using the recombinant DNA techniques (Huse et al. 1989).

Monoclonal antibodies may also be made by immunizing the suitable animals with a unpurified preparation of the polypeptide of the invention. The resulting hybridoma clones secreting monoclonal antibodies should be screened for their ability to binding to polypeptide(s) or its analogue.

For purposes not requiring a high specificity, the antibody may be a polyclonal antibody. Polyclonal antibodies may be obtained, e.g. as described in Harboe and Ingild, see above. More specifically, when polyclonal antibodies are to be obtained, the polypeptide of the invention or an analogue thereof is, preferably after addition of a suitable adjuvant, such as Freund's incomplete or complete adjuvant, injected into an animal. The animals are bled regularly, for instance at weekly intervals, and the blood obtained is separated into an antibody containing serum fraction, and optionally said fraction is subjected to further conventional procedures for antibody purification, and/or procedures involving use of the purified polypeptide or an analogue thereof.

The antibody may also be an anti-anti-idiotypic antibody directed against an anti-idiotypic antibody which is an antibody directed against the site of an antibody which is reactive with the epitope on the antigen. The anti-idiotypic antibody may be prepared by a similar method to that outlined above for the monoclonal or polyclonal antibody.

Within the scope of the invention is an antibody which binds to a substance or polypeptide as defined above, in particular an antibody which binds specifically to a polypeptide having the amino acid sequence Ala-Tyr-Met-Thr-Met-Lys-Ile-Arg-Asn (SEQ ID NO:1).

In a broad aspect, the invention thus relates to a substance which is capable of neutralizing one or more of the hIL-10 activities a) to j), i.e. having hIL-10 antagonist activity, such as an antibody having these properties. A monoclonal antibody 19F1 (82) which is capable of specifically binding to IL-10 is known and can block endogenous IL-10 produced by LPS stimulated monocytes, see Table 1 (82). This antibody recognizes the natively folded IL-10, but not necessarily a whole functional domain; however, this antibody does not specifically bind IT9302.

Within the scope of the present invention is also a pharmaceutical composition comprising a such substance as well as a pharmaceutical composition comprising a substance or polypeptide of the invention.

A very important aspect of the invention relates to a pharmaceutical composition comprising a substance having hIL-10 agonist activity or hIL-10 antagonist activity as defined above and a pharmaceutically acceptable excipient. The composition may comprise e.g. purified synthesized protein or a purified recombinant polypeptide, a monoclonal or polyclonal antibody or any other substance fulfilling the criteria a)–j) or, if having hIL-10 antagonist activity, being capable of neutralizing one or more of the hIL-10 activities a) to j).

The IL-10 agonist or antagonist used in this invention may be prepared as formulations in pharmaceutically acceptable media, for example, saline, phosphate buffered saline (PBS), Ringer's solution, dextrose/saline, Hank's solution, and glucose. The compositions may contain pharmaceutically acceptable auxiliary substances as required to approximate physiological conditions, such as buffering agents, tonicity adjusting agents, wetting agents, detergents, and the like. Additives may also include additional active ingredients, e.g. bactericidal agents, or stabilizers. The amount administered to the patient will vary depending upon what is being administered, the purpose of the administration, such as prophylaxis or therapy, the state of the host, the manner of administration, and the like.

The pharmaceutical compositions are typically intended for transdermal or parenteral administration, e.g. intravenously, subcutaneously, or intramuscularly. Orally administrative forms are also desired and can be provided by modifying the composition to bypass the stomach environment. The composition can be used for prophylactic and/or therapeutic treatment. Preferably, the pharmaceutical compositions are administered intravenously. Thus, the invention provides compositions which comprise an IL-10 agonist or antagonist substance dissolved or suspended in an acceptable carrier, preferably an aqueous carrier. These compositions may be sterilized by conventional sterilization techniques, or may be sterile filtered.

The resulting aqueous solutions may be packaged for use as is, or lyophilized, the lyophilized preparation being combined with a sterile aqueous carrier prior to administration. The IL-10 agonist or antagonist may also be administered with a second biologically active agent, such as a standard chemotherapeutic agent. Such agents include but are not limited to vincristine, daunorubicin, L-asparaginase, mitoxantrone and amsacrine.

In therapeutic applications, the pharmaceutical compositions are administered to a patient in an amount sufficient to produce the desired effect, defined as a "therapeutically effective dose". The therapeutically effective dose of a IL-10 agonist or antagonist will vary according to, for example, the particular use for which the treatment is made, the manner of administration, the health and condition of the patient, and the judgment of the prescribing physician. For example, the dose for continuous infusion will typically be in the range of about 500 ng to about 800 μg per day for a 70 kg patient, preferably between about 10 μg and about 300 μg. The dose will typically be between 700 ng/kg/day and 16 μg/kg/day.

The concentration of IL-10 agonist or antagonist in the pharmaceutical formulations can vary widely, i.e. from about 10 μg to about 5 mg/ml, preferably between about 100 μg and about 2 mg/ml. The concentration will usually be selected primarily by fluid volumes, viscosities, etc., in accordance with the particular mode of administration selected. Thus, a typical pharmaceutical composition for intravenous infusion could be made up to contain 250 ml of dextrose/saline solution and 2.5 mg of IL-10 agonist or antagonist.

For solid compositions, conventional non-toxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable non-toxic composition is formed by incorporating normally employed excipients, such as those carriers previously listed, and generally 10–95% of active ingredient, that is, an IL-10 agonist or antagonist substance, preferably 25–75%.

For aerosol administration, the IL-10 agonist or antagonist is preferably supplied in finely divided form along with a surfactant and propellant. Typical percentages of IL-10 agonist or antagonists are 0.01–20% by weight, preferably 1–10%. The surfactant must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arbitol, mannitol, sorbitol, the hexitol anhydrides derived from sorbitol, and the polyoxyethylene and polyoxypropylene derivatives of these esters. Mixed esters, such as mixed or natural glycerides may be employed.

The surfactant may constitute 0.1–20% by weight of the composition, preferably 0.25–5%. The balance of the composition is ordinarily propellant. Liquified propellants are typically gases at ambient conditions, and are condensed under pressure. Among suitable liquified propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided polypeptide(s) and surfactant. The ingredients are thus maintained at an elevated pressure until released by action of the valve.

To enhance the serum half-life, the IL-10 agonist or antagonist may be encapsulated, introduced into the lumen of liposomes, prepared as a colloid, or other conventional techniques may be employed which provide an extended lifetime of the polypeptides. Thus, in certain embodiments, the IL-10 agonist or antagonist may be encapsulated in a liposome. A variety of methods are available for preparing liposomes, as described in, e.g., (83), (84), (85) and (86).

One important embodiment of the invention thus relates to the use of a substance for diminishing or neutralizing high concentration of hIL-10 and/or vIL-10, such as the use of a substance having hIL-10 antagonistic properties for the manufacture of a pharmaceutical composition for the treatment or prophylaxis of ovary cancer and/or AIDS (87, 19).

Within the scope of the invention is also a method of treating and/or preventing ovary cancer and/or AIDS, the method comprising administering, to a patient in need thereof, a therapeutically or prophylactically effective amount of a hIL-10 antagonist substance as well as use of a compound which has an hIL-10 antagonist activity for the manufacture of a pharmaceutical composition for treatment or prophylaxis of ovary cancer and/or AIDS.

Use of the Substance According to the Present Invention

In accordance with the present invention, it has as described above been found that IT9302 and analogues and variants thereof are useful for preventing effects of cytokines known to be pathogenetically involved in the previously described pathological conditions.

Therefore, the potentials of therapy by using the polypeptide of the invention or analogues or derivatives thereof is contemplated and should be investigated in all diseases where a therapeutic effect of hIL-10 and/or IRAP is expected (see above, Table 3).

Very important embodiments of the invention relate to use of a substance or polypeptide of the invention for the treatment or prophylaxis of one or more of the diseases mentioned in Table 3, to the use of a substance or polypeptide according to the invention for the manufacture of a pharmaceutical composition for the treatment or prophylaxis of one or more of the diseases mentioned in Table 3, as well as to a method of treating and/or preventing one or more of the diseases mentioned in Table 3, the method comprising administering to a patient in need thereof a therapeutically or prophylactically effective amount of a substance or polypeptide according to the invention.

One important aspect of the invention is thus the use of IT9302 or a functional derivative thereof for the manufacture of a pharmaceutical composition for substantially inhibiting a biological effect in a human related to a cytokine, such as a lymphokine, interleukin, monokine, chemokine, interferon, colony-stimulating factor, prostaglandin and/or leukotriene, for the prophylaxis or treatment of a condition related to a disturbance of a cytokine system such as the lymphokine, interleukin, monokine, chemokine, interferon or colony-stimulating factor system and/or a disturbance in the prostaglandin and/or leukotriene system. As used herein, the term "pharmaceutical composition" comprises any composition suitable for human use as described in detail above.

The invention particularly relates to the use of IT9302 or a functional derivative thereof for substantially inhibiting a biological effect in a human related to a cytokine for the prophylaxis or treatment of a condition related to a disturbance of a cytokine system; and/or for substantially inhibiting a biological effect in a human related to a lymphokine for the prophylaxis or treatment of a condition related to a disturbance of a lymphokine system; and/or for substantially inhibiting a biological effect in a human related to a interleukin for the prophylaxis or treatment of a condition related to a disturbance of a interleukin system; and/or for substantially inhibiting a biological effect in a human related to a monokine for the prophylaxis or treatment of a condition related to a disturbance of a monokine system; and/or for substantially inhibiting a biological effect in a human related to a chemokine for the prophylaxis or treatment of a condition related to a disturbance of a chemokine system; and/or for substantially inhibiting a biological effect in a human related to a lymphokine for the prophylaxis or treatment of a condition related to a disturbance of a lymphokine system; and/or for substantially inhibiting a biological effect in a human related to an interferon for the prophylaxis or treatment of a condition related to a disturbance of an interferon system; and/or for substantially inhibiting a biological effect in a human related to a colony-stimulating factor for the prophylaxis or treatment of a condition related to a disturbance of a colony-stimulating factor system; and/or for substantially inhibiting a biological effect in a human related to a prostaglandin for the prophylaxis or treatment of a condition related to a disturbance of a prostaglandin system; and/or for substantially inhibiting a biological effect in a human related to a leukotriene for the prophylaxis or treatment of a condition related to a disturbance of a leukotriene system.

LEGENDS TO FIGURES

FIG. 1 shows a comparison of the predicted amino acid sequences of mIL-10 (SEQ ID NO:24), hIL-10 (SEQ ID NO:25), and BCRFI (SEQ ID NO:26). Amino acid sequence identities ties are indicated by vertical lines.

FIG. 2 shows the COOH terminal polypeptide sequences of IL-10 including 9 amino acids and comparing porcine (SEQ ID NO:27), human (SEQ ID NO:1), BCRFI (last nine residues of SEQ ID NO:26) and mouse proteins (last 9 residues of SEQ ID NO:24) proteins.

Figure 12:
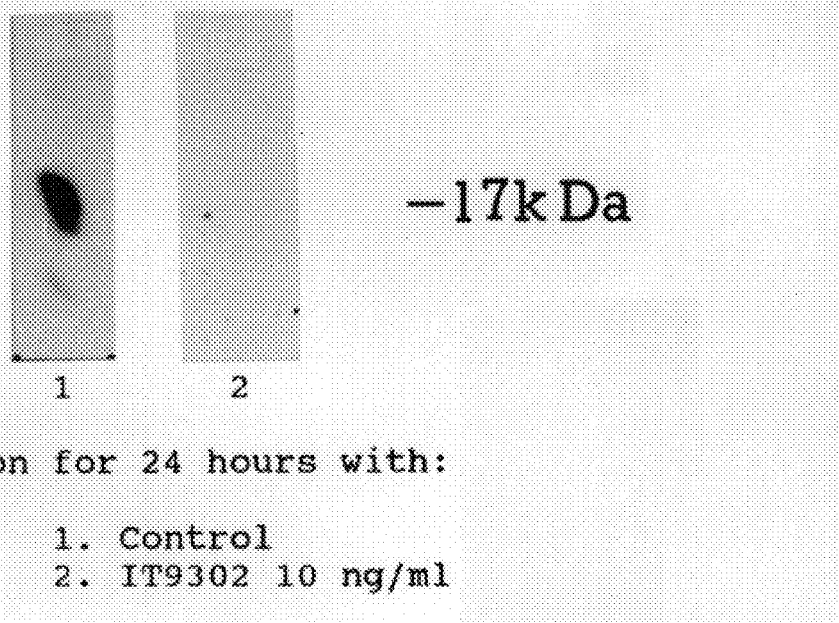

FIG. 12 shows TNF-α production in human mixed lymphocyte culture cytosolic fractions by ECL-Western Blotting. TNF-α Western Blotting was carried out as the IL-4 described in Materials and Methods, but using a rabbit anti-human TNF-α antibody (Pepro Tech. Inc., London, England) and a horseradish peroxidase-labelled secondary antibody (Cat.no. P 217, Dako, Denmark).

Figure 13:
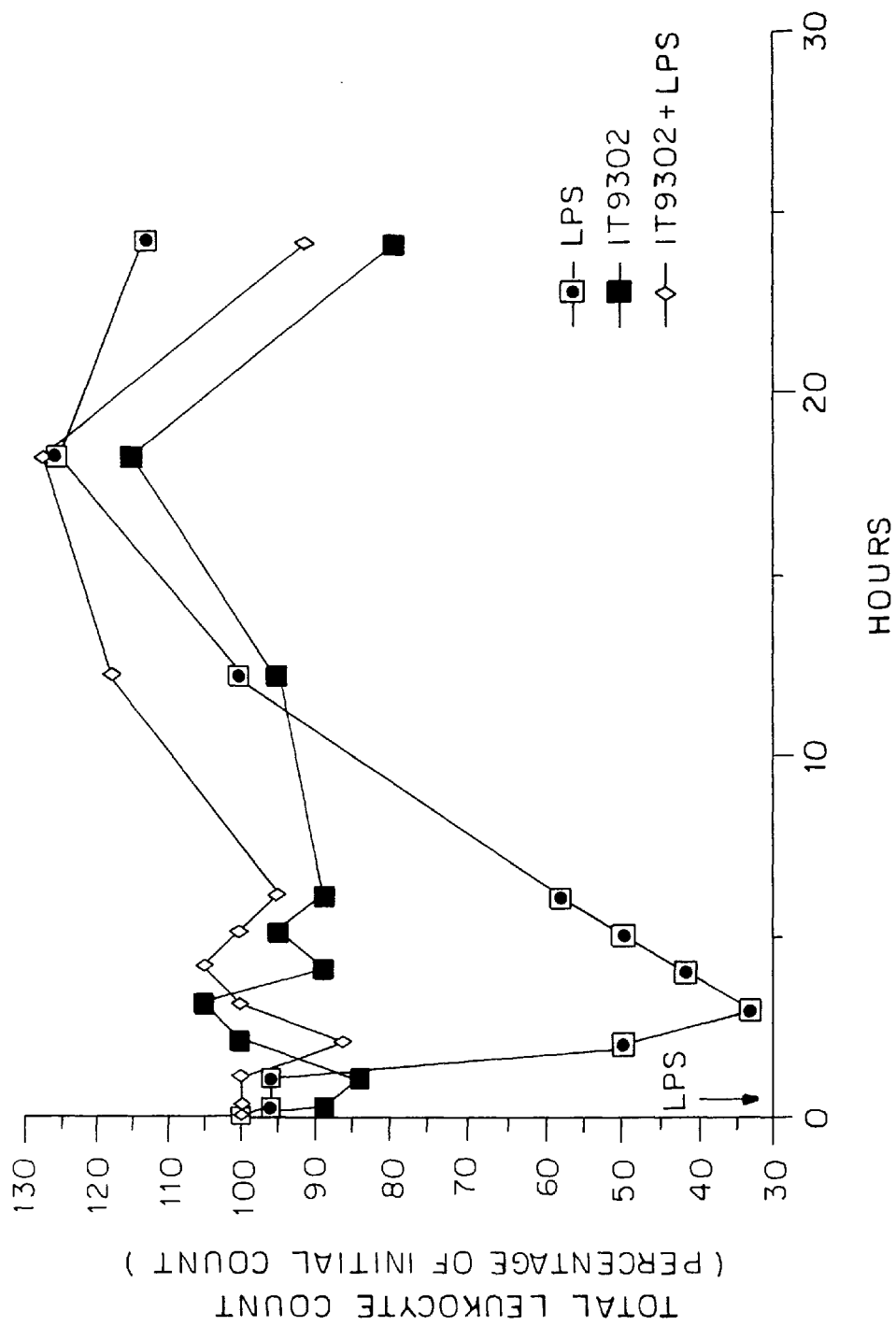

FIG. 13 shows that LPS induced shock and leukopenia are modulated by IT9302, shown by total leukocyte counting.

The drawing shows the effect of IT9302 on LPS induced "septic" leukocytopenia. IT9302 was injected 30 minutes before LPS injection.

EXAMPLES

Materials and Methods

Cytokines and Chemoattractants

Recombinant hIL-10 was obtained from Pepro Tech Inc., N.J. (Cat.No. 200 10). Recombinant hIL-1β and recombinant hIL-8 were a kind gift from Dainippon Pharmaceutical Company, Osaka, Japan. The culture medium was RPMI 1640 GIBCO, LPS-free according to the Limulus Amoebocyte Lysate assay (Sigma E-TOXATE Kit Cat.No. 210-A1). rhMCAF/MCP-1 was a kind gift from professor Kouji Matsushima, Kanazawa, Japan.

Leukocyte Chemotaxis Assay

T Cell Chemotaxis

CD4+ and CD8+ T lymphocyte subsets characterized by expressing either CD4 or CD8 antigens were purified from heparinized blood of normal donors. Thus, peripheral blood mononuclear cells (PBMC) were purified from the heparinized blood by diluting 100 ml of the blood with Hanks balanced salt solution (HBSS) 1:1 and then separated by layering the cells on Lymphopac™ (Nycomed Pharma, Oslo, Norway) followed by gradient centrifugation at 2000 rpm for 20 minutes. The mononuclear cells were washed 3 times in HBSS and the cell pellet was diluted in 4 ml of HBSS containing 1% fetal calf serum and sorted at 4° C. by using Dynabeads coated with monoclonal antibody towards CD4 or CD8 antigen (Dynabeads M-450 CD4 Cat.No. 111.16, Dynabeads M-450 CD8 Cat.No. 111.08, DETACHa-BEAD Cat.No. 125.04). The bead:cell ratio was 10:1 and the incubation time 1 hour. The beads were detached by adding polyclonal anti-mouse antibody according to the manufacturer's instructions.

The chemotaxis assay was a 48-well micro chamber technique (Neuroprobe, Rockville, Md.) as previously described (74; see ref. 3 and ref. 14). Chemoattractants were diluted in RPMI 1640 (GIBCO Cat.No. 61870-010) with 1% sterile filtered fetal calf serum and placed in the lower 25 μl chamber. In the case of determining T cell chemotaxis, T cells ($5 \times 10^6$/ml) were suspended in medium and 50 μl was placed in the upper chamber separated from the lower chamber by a 5 μm pore-size polycarbonate, polyvinylpyrrolidone-free filter (Nucleopore Corp., Pleasanton, Calif.) coated with type IV collagen (Sigma Cat.No. C 0543). Cells were allowed to migrate for 2 hours at 37° C. at 5% $CO_2$. The filters were then carefully removed, fixed in 70% methanol, and stained for 5 minutes in Coomassie's Brilliant Blue. Cells attached to the lower surface of the filter were counted by measuring their area using a video camera on the microscope connected to a computer system for digital analysis and supported by software for objective determination of chemotactic migration. Approximately 5% of the T cells will migrate spontaneously corresponding to between 12,000 and 13,000 cells; this may vary from day to day, but very little in the same day's experiments. As has been described earlier (ref. 3 and ref. 14), it was therefore chosen to report the results as a ratio between number of cells migrating in the sample and in the negative control, which reflects spontaneous migration. This ratio is referred to as the chemotactic index (CI). All samples were analyzed in triplicates and cell migration in each well was measured in three fields before the median value of area was estimated. In some experiments the chemotaxis membrane was not coated with collagen, and in the present assay system migrating cells will therefore drop to the bottom of the lower well of the chemotaxis chamber.

In one experiment, the chemotactic activity of IT9302 on CD8+ T cells was performed by testing serial dilutions of IT9302 added to the lower chamber and evaluating chemotaxis as described above.

In a second experiment, the ability of IT9302 to desensitize the migration of CD8+ T cells as a response to rHIL-10 (10 ng/ml) was studied by adding IT9302 to the target cells 30 minutes before chemotaxis. IT9302 was added in serial concentrations and the chemotactic response of rhIL-10 was evaluated as described above.

In a third experiment, the ability of IT9302 to suppress the chemotactic response of CD4+ T cells towards rhIL-8 (10 ng/ml) was studied by adding IT9302 to the target cells 30 minutes before performing chemotaxis. IT9302 was added in serial concentrations and the chemotactic response of rhIL-8 was evaluated as described above.

Monocyte Chemotaxis

Monocyte chemotaxis was measured using the same Boyden chamber equipment as described for T cells above. The chemo-attractant MCAF/MCP-1 was diluted in RPMI 1640 medium with 0.5% BSA and added to the lower chamber at a concentration of 10 ng/ml. Monocytes, purified by the standard plastic adherence technique, from normal human PBMC, obtained as described above were suspended in RPMI 1640 medium with 0.5% BSA and then incubated for 30 minutes in the presence of IT9302 at different concentrations. Subsequently, the cells were added to the upper chemotaxis chambers at a concentration of $10^6$ cells/ml. The upper and lower chambers were separated by an 8 $\mu$m pore size polyvinyl pyrrolidone-free polycarbonate filter (Nucleopore, Pleasanton, Calif., The chamber was incubated at 37° C. for 90 minutes. The membranes containing migrating cells were treated as described above and a chemotactic index calculated according to the technique described above.

Production of IL-8 by Normal Human Peripheral Mononuclear Cells (PBMC)

PBMC was purified from heparinized blood of normal human donors. Following gradient centrifugation with Lymphoprep™ (Nycomed Pharma, Oslo, Norway), the mononuclear cells were diluted to $2 \times 10^6$ cells/ml in LPS-free RPMI 1640 medium (Gibco Cat.No. 6187-010) containing 1% sterile filtered heat-inactivated fetal calf serum and penicillin (10,000 IE/ml), streptomycin (10 mg/ml) and gentamycin (2.5 mg/ml). Cells were cultured in 24 wells Nunc Micro Plates (Nunc, Denmark) and in the presence of different concentration of IT9302 (0, 1 $\mu$g, 100 ng, 10 ng, 1 ng, 0.1 ng, 0.01 ng/ml) for 24 hours. Following 24 hours of incubation, another dose of IT9302 was added once more, and 1 hour later r-hIL-1$\beta$ (1 ng/ml) was added to the cell cultures. Supernatants were collected after a total of 48 hours of incubation, and the concentration of the secreted IL-8 was measured by IL-8 ELISA by using an IL-8 ELISA Kit (Dainippon Pharmaceutical Co. Ltd, Osaka, Japan). Briefly, standards and cell supernatants were incubated for one hour and in duplicates at 20° C. on a micro-plate shaker. Then after washing, a second antibody was added for one hour, followed by one hour of incubation with peroxidase-labelled goat anti-rabbit IgG. After washing, the reaction was developed with O-phenylenediamine. Thirty minutes later the reaction was stopped with 1.6 N sulphuric acid. Optical density (OD) was measured in an ELISA reader at 490 nm. IL-8 concentration was calculated by a calibration curve of absorbance of unknown vs concentrations of IL-8 standards.

Determination of IRAP Concentration

PBMC was purified as described above. PBMC was cultured in RMPI 1640, 10% sterile heat-inactivated fetal calf serum (including penicillin 10,000 IE/ml, streptomycin 10 mg/ml, gentamycin 2.5 mg/ml) and the cell concentration was $5 \times 10^6$ cells/ml. The monocytes were then purified by standard plastic adherence technique. Monocytes were then cultured in RPMI 1640 with 2% FCS ($2.5 \times 10^6$ cells/ml) and with different dilutions of rhIL-10 or IT9302. The cells were stimulated for 24 hours and the supernatants were collected for IRAP determination. IRAP ELISA was carried out by using Human IL-1ra Quantikin Immunoassay Kit from R&D Systems Europe Ltd. (Cat.No. DRA 00, Abingdon, Oxon, UK).

Determination of Class II MHC Antigen Expression on Monocytes

PBMC was purified as described above and monocytes isolated by plastic adherence technique. Monocytes were then cultured in RPMI 1640 with 2% FCS including penicillin 10,000 IE/ml, streptomycin 10 mg/ml, gentamycin 2.5 mg/ml at a cell concentration of $3 \times 10^6$/ml. Cells were stimulated for 40 hours in microwells (Nunc, Denmark) with 100 ng/ml rhIL-10, or IT9302 1 $\mu$g/ml, 100 ng/ml, 10 ng/ml. At the end of stimulation, the supernatants were removed and the cells were detached from the plastic by freezing at $-20°$ C. for 20 minutes. The cells were collected in 1 ml of cold HBSS with 1% FCS and sorted at 20° C. by using 50 $\mu$l/ml Dynabeads M 450 coated with monoclonal antibody for HLA class II $\beta$ chain (Cat. No. 210.03). After 20 minutes of incubation, the cells were washed 3 times with cold HBSS with 1% FCS and collected on a magnetic separation device. The cells were diluted in the above buffer and stained with methylene blue, and the resetting cells (cells carrying Dynabeads with HLA class II mAb) were counted.

Determination of IL-4 Production by CD4+ T Lymphocytes Cell Cultures

CD4+ T lymphocytes were purified from heparinized normal human blood. Following Lymphoprep™ (Nycomed Pharma, Oslo, Norway) gradient centrifugation, the mononuclear cells were further sorted at 4° C. using Dynabeads (Dynal AS, Norway) coated with monoclonal anti-CD4 antibodies. The beads were detached by adding polyclonal anti-mouse antibody (Dynal AS, Norway). The purity of the positively selected cells were higher than 99% as judged by FACS analysis. When examining the de novo production of IL-4 by IL-8-stimulated T cells, T cells were cultures, $5 \times 10^6$ cells/ml in LPS-free RPMI 1640 (Gibco Cat.no. 61870-010) containing 1% sterile-filtered, heat-inactivated fetal calf serum (FCS), penicillin (10,000 IU/ml), streptomycin (10 mg/ml) and gentamycin (2.5 mg/ml).

T cells were stimulated for 3 days using rIL-8 (100 ng/ml), rIL-10 (100 ng/ml), IT9302 (10 ng/ml) and IFN-$\gamma$ (10 ng/ml). Recombinant human IL-8 (rh IL-8) was a kind gift from Dainippon Pharmaceuticals Co. Ltd., Osaka, Japan), and IFN-$\gamma$ was purchased from Boehringer Ingelheim Am Rhein, Germany. To obtain specific inhibition of IL-8 stimulation, a neutralizing monoclonal anti-IL-8 antibody (WS.4) was used (a kind gift from Dr. K. Matsushima, Japan). Recombinant IL-10 was purchased from Pepro Tech. Inc. (London, England).

Preparation of Cell Material and Culture Supernatant for Gel Electrophoresis

Cultured T cells and culture media were separated by centrifugation at 2000 rpm for 5 minutes. The supernatants were freeze-dried and then dissolved in 100 $\mu$l of lysis buffer. The cells were resuspended directly in 100 $\mu$l of gel lysis buffer (9). The material was kept at $-80°$ C. until further examination.

ECL-Western Blotting of CD4+ T Cell Derived Proteins

Cells or freeze-dried cell culture supernatants were used for IL-4 protein content determination. Proteins from onedimensional 15% SDS-PAGE gels were transferred by blotting onto Hybond-ECL nitrocellulose membranes (Amersham RPN 2020D, UK) and blocked with 5% bovine serum albumin (Sigma) in Tris buffer saline pH 7.8 containing 0%. Tween-20. The blots were then incubated with a polyclonal goat anti-human IL-4 antibody (R&D Systems, UK) followed by a horseradish peroxidase-labelled secondary antibody (Cat.no. RPN 2106 ECL, Amersham, UK), and the immunostaining was detected by exposing a film (Kodak X-OMAT-S, U.S.A) for 90 seconds.

Specificity of IT9302 Amino Acid Sequence

Searching for possible homology of the IT9302 sequence with other known proteins was carried out by searching on the EMBO protein database kindly assisted by Dr. Henrik Leffers, Institute for Medical Biochemistry, University of Aarhus, Denmark.

Amino Acid Sequence Specificity of IT9302

According to information from the EMBO protein database (Heidelberg) performed on Jun. 10, 1994, IT9302 has 100% homology with a sequence of the human IL-10 and 75% with a sequence of an Epstein-Barr virus derived protein identical with vIL-10. Other virus proteins as phage T7 and tomato yellow leaf curl virus revealed 75% and 85% identity, respectively.

Results

The conception of the invention took place in October and November 1992, when a nonapeptide designated IT9302 was designed according to the strategy outlined above, and the chemical synthesis of the first prototype (IT9302) was decided and ordered on Nov. 27, 1992. It was expected that this nonapeptide should exert immunomodulatory activities of which some would mimic IL-10-like activity, and the following control experiments (examples) were planned during this period as well. The chemical synthesis of IT9302 was carried out by using an automatic polypeptide synthesizer performed by Carlbiotech Ltd. A/S, Denmark as a payed order by the inventors. Afterwards the protein was purified on HPLC and the purity confirmed to exceed 95% by HPLC. This confirmed that the synthesized product was identical with the IT9302 designed by the inventors in October and November 1992.

Example 1

IT9302 Induced Inhibition of Spontaneous IL-8 Production by Human Monocytes

Figure 3:
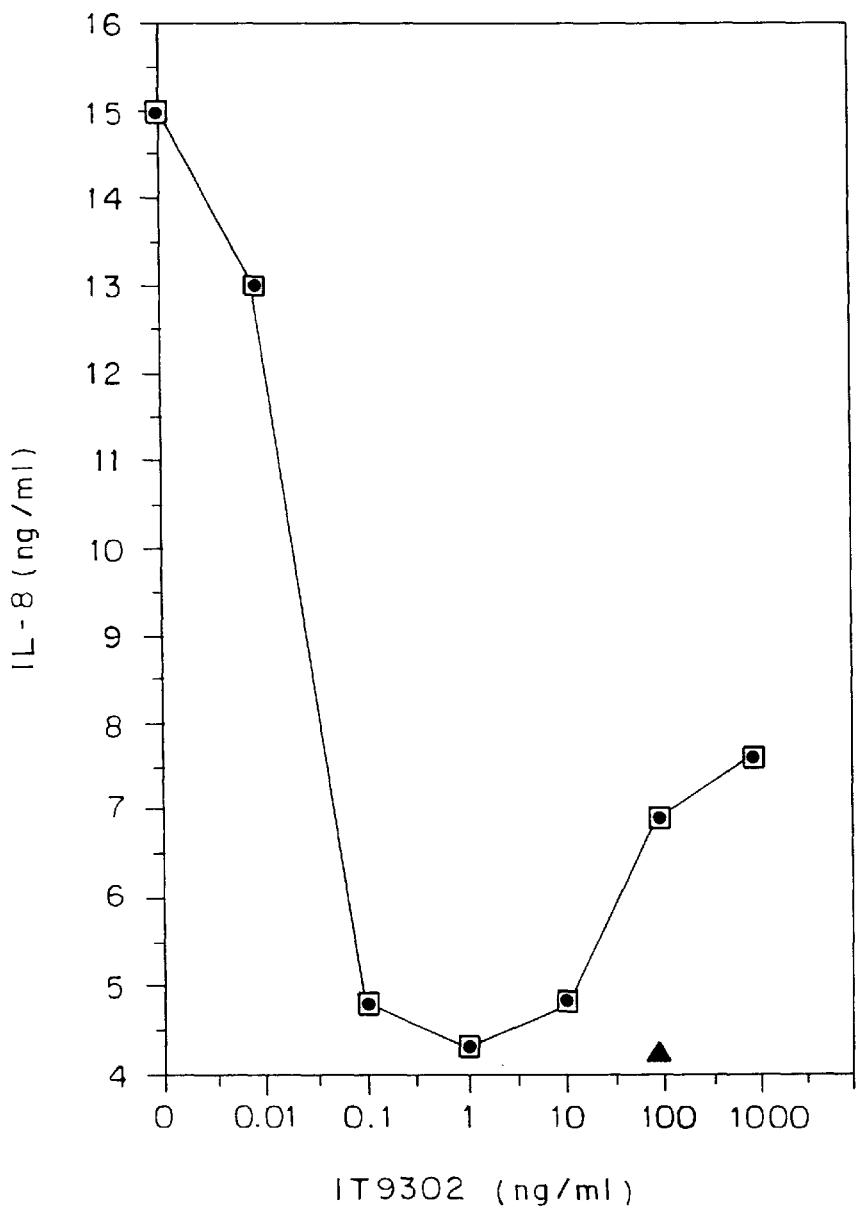
FIG. 3 is a diagram showing that IT9302 inhibits spontaneous IL-8 production by purified cultured human monocytes.

The test was performed as described in "Production of IL-8 by normal human peripheral mononuclear cells (PBMC)". Monocytes were purified by plastic adherence technique and $3.0 \times 10^6$ cells/ml were stimulated for 40 hours. As shown in FIG. 3, IT9302 inhibited the production of IL-8 by monocytes, and at 0.1 ng/ml of IT9302 the IL-8 production was suppressed to 35% of the spontaneous production in vitro. The viability of cells always exceeded 80% after 1 day in culture and the addition of IT9302 did not in this or in the following examples affect viability at any concentration of IT9302 between 0.1 and 1000 ng/ml (IT9302 MW: 1,127 dalton, rhIL-10 predicted MW: 18,400 dalton).

Example 2

IT9302 Induced Inhibition of IL-1β Induced IL-8 Production by Human Peripheral Blood Mononuclear Cells (PBMC)

Figure 4:
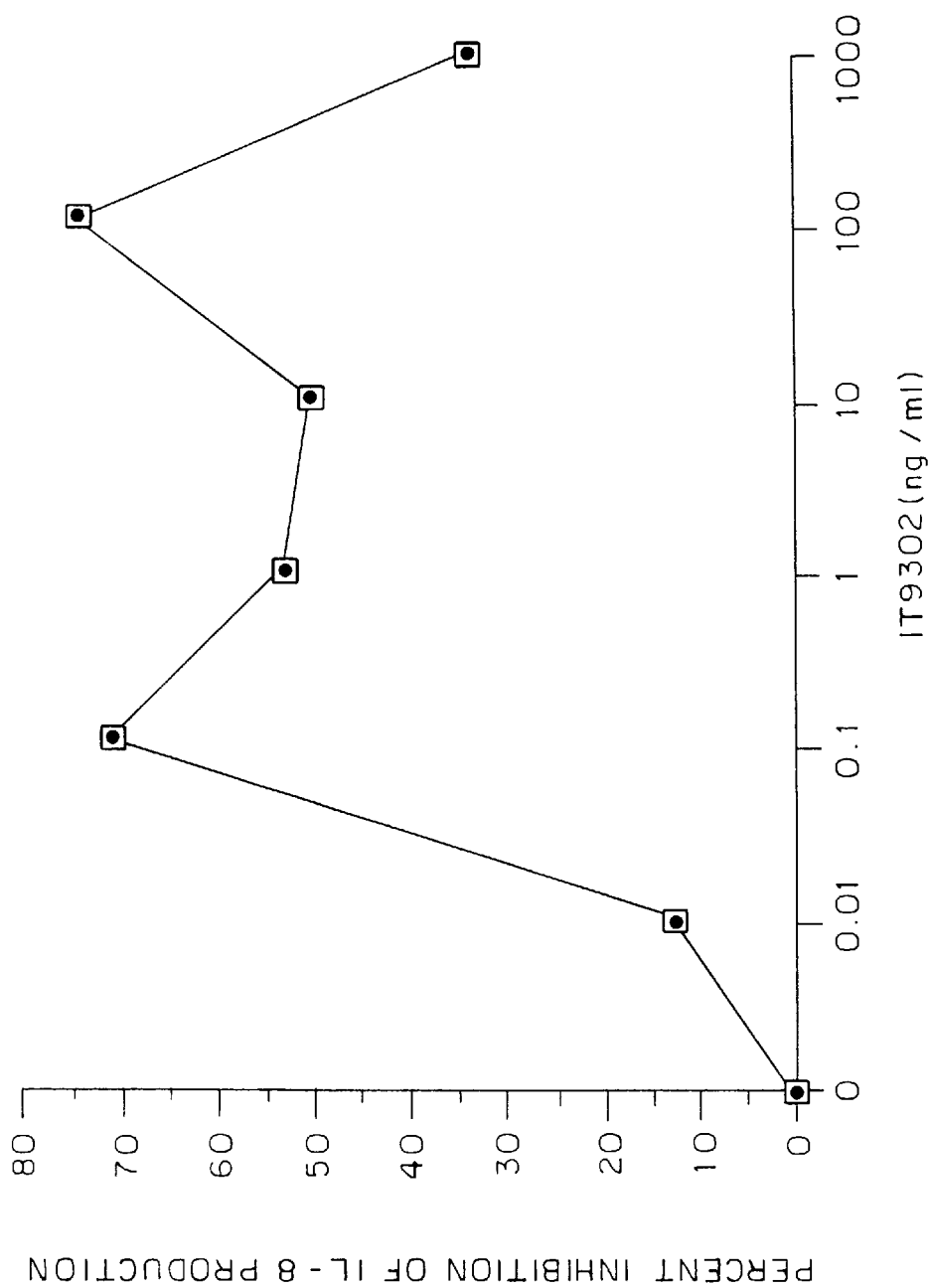
FIG. 4 is a diagram showing that IT9302 inhibits IL-1 induced (1 ng/ml) IL-8 production by human peripheral blood mono-nuclear cells.

The test was performed as described in "Production of IL-8 by normal human peripheral blood mononuclear cells (PBMC)". As shown in FIG. 4, IT9302, in a dose dependent manner, inhibited the IL-1β induced production of IL-8 by human peripheral blood mononuclear cells in vitro. The suppression of IL-8 production plateaued at IT9302 concentrations between 0.01 and 100 ng/ml.

Example 3

Figure 5:
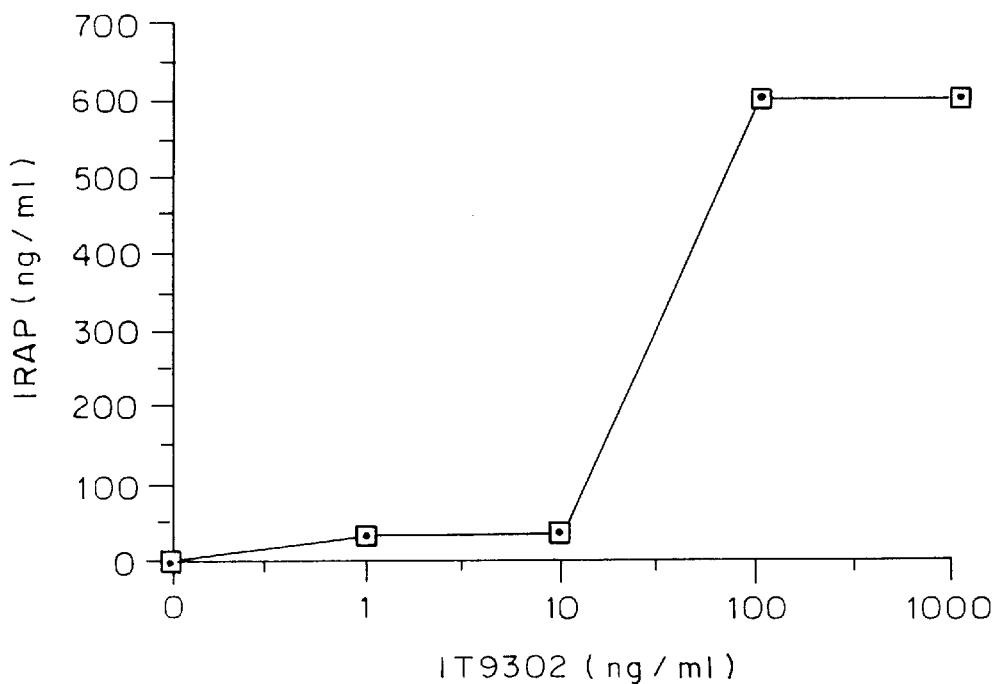
FIG. 5 illustrates IRAP production by IT9302-stimulated human monocytes.
Figure 6:
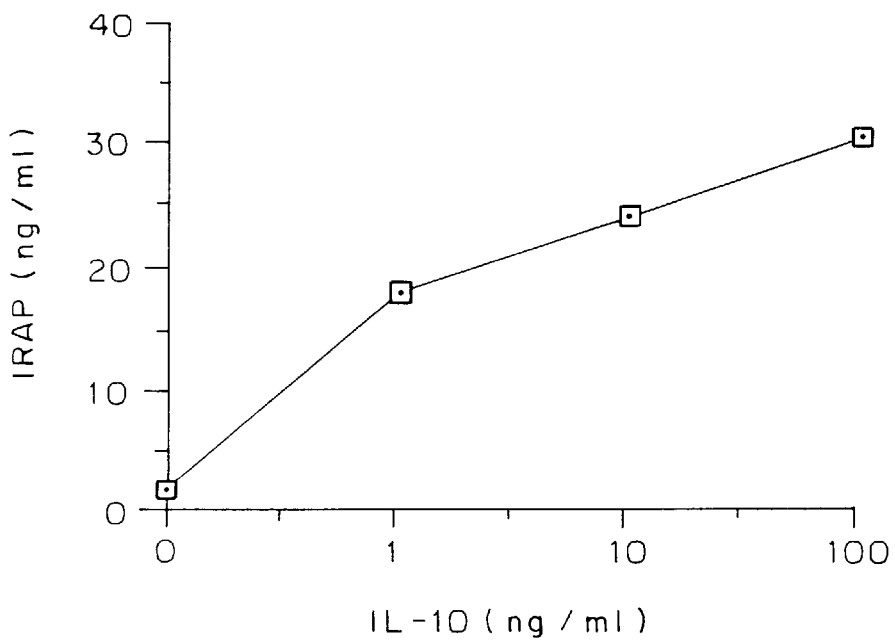
FIG. 6 illustrates IRAP production by IL-10-stimulated human monocytes.

IT9302 Induced Production of Interleukin-1 Receptor Antagonist Protein (IRAP) by Human Monocytes The test was performed as described in "Determination of IRAP concentration". As shown in FIG. 5, IT9302 dose-dependently induced the production of IRAP by human monocytes. The production drastically increased when using concentrations of IT9302 above 10 ng/ml. FIG. 6 shows the induction of IRAP by rhIL-10 and since hIL-10 is approximately 20 times larger than IT9302, 10 ng/ml of IT9302 equals 200 ng/ml of IL-10 in molarity. Therefore the potencies of IT9302 and rhIL-10 are comparable and approximately equal with respect to the induction of IRAP at lower concentrations. At IT9302 concentrations exceeding 10 ng/ml, the induction of IRAP drastically increased and reached levels of approximately 700 ng/ml.

Example 4

The Chemotactic Effect of IT9302 on Human CD8+ T Lymphocytes

Figure 7:
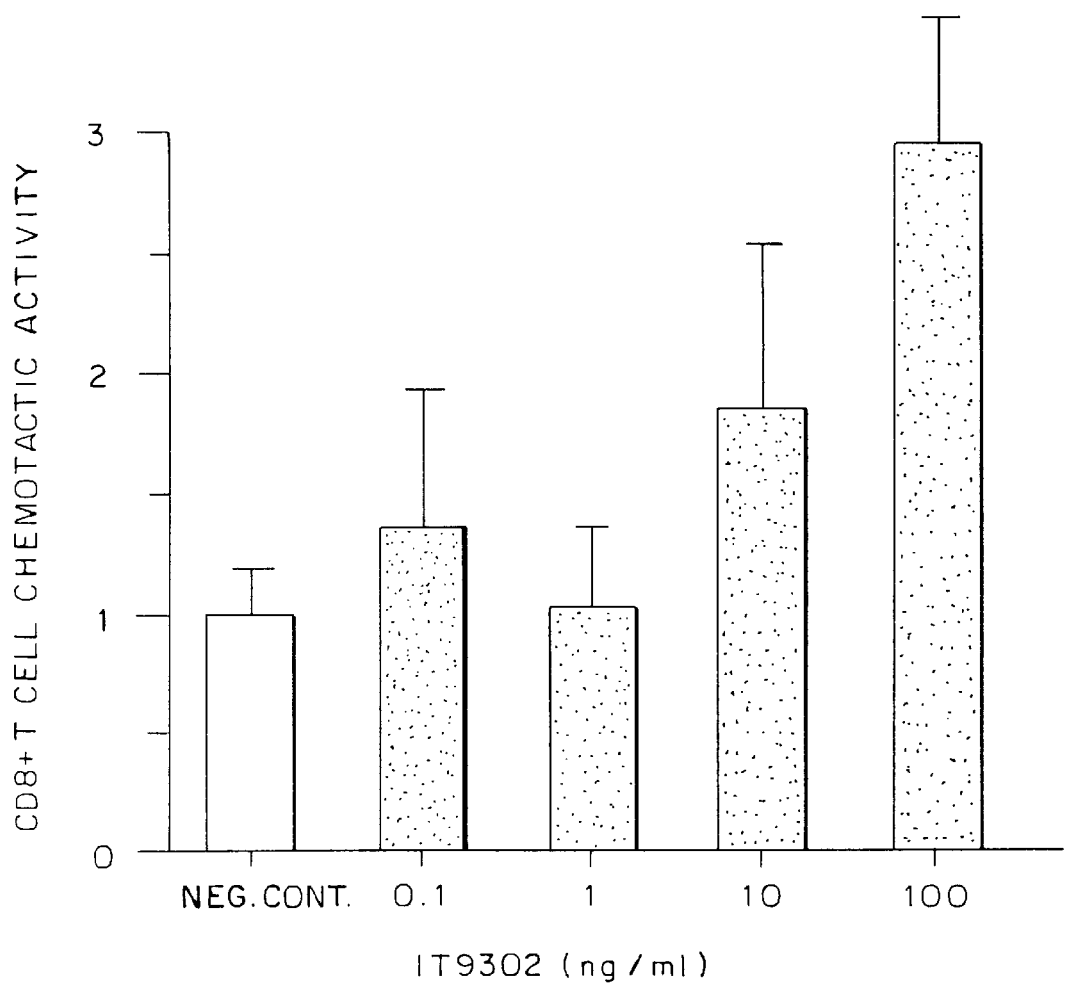
FIG. 7 illustrates the chemotactic activity of IT9302 on CD8+ T cells

The experiment was carried out as described in "Leukocyte chemotaxis assay". As shown in FIG. 7, IT9302 induced the chemotactic migration of CD8+ human T lymphocytes in vitro, while there was no effect on CD4+ T cells (data not shown). Again, the potency of IT9302 shown in this experiment is comparable with that of rhIL-10 shown previously (ref. 14).

Example 5

IT9302 Desensitizes Human CD8+ T Cells Resulting in an Unresponsiveness Towards rhIL-10

Figure 8:
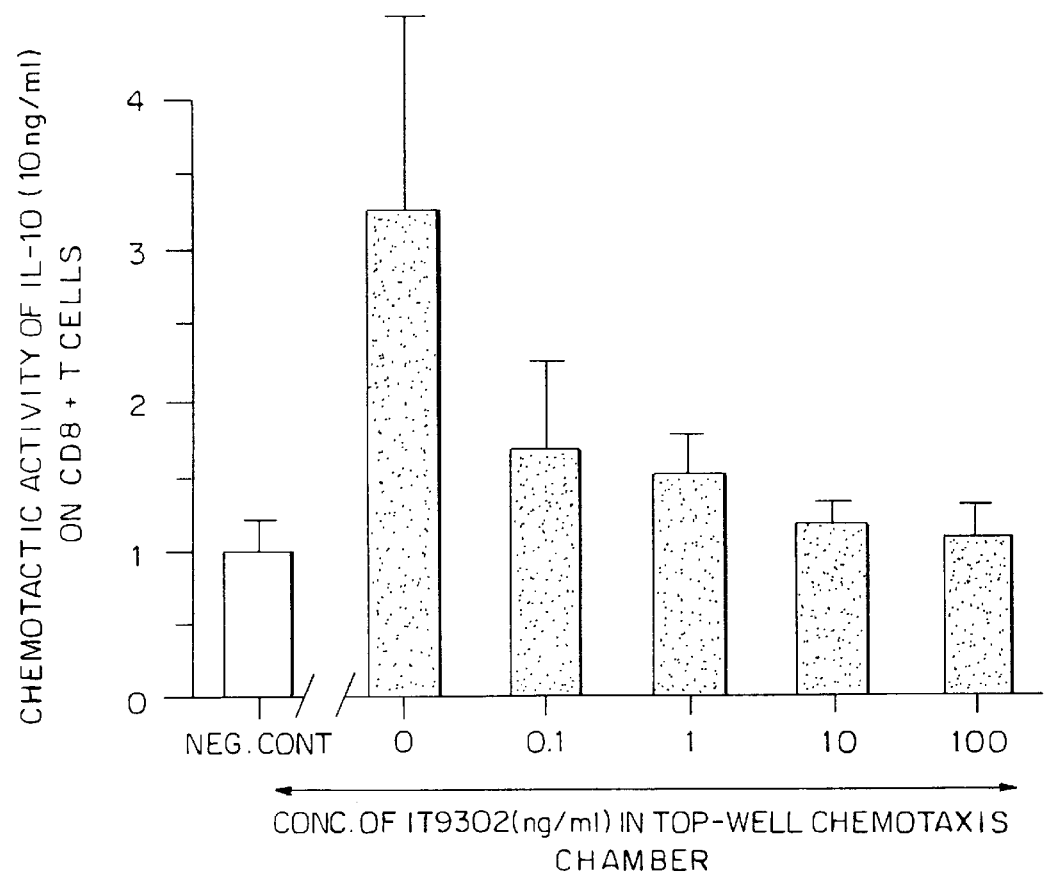
FIG. 8 illustrates the desensitization of DC8+ T cells by IT9302, resulting in unresponsiveness of CD8+ T cells towards IL-10 (10 ng/ml) induced chemotaxis.

The experiment was carried out as described in "Leukocyte chemotaxis assay". IT9302 was added to a suspension of CD8+ T cells 30 minutes before these cells were tested towards their chemotactic response to rhIL-10. As shown in FIG. 8, the pre-incubation of cells with IT9302 results in a suppressed responsiveness of the CD8+ T cells towards hrIL-10. This indicates that IT9302 may affect the binding of rhIL-10 to the IL-10 receptor.

Example 6

IT9302 Suppresses the Chemotactic Response of CD4+ T Lymphocytes Towards IL-8

Figure 9:
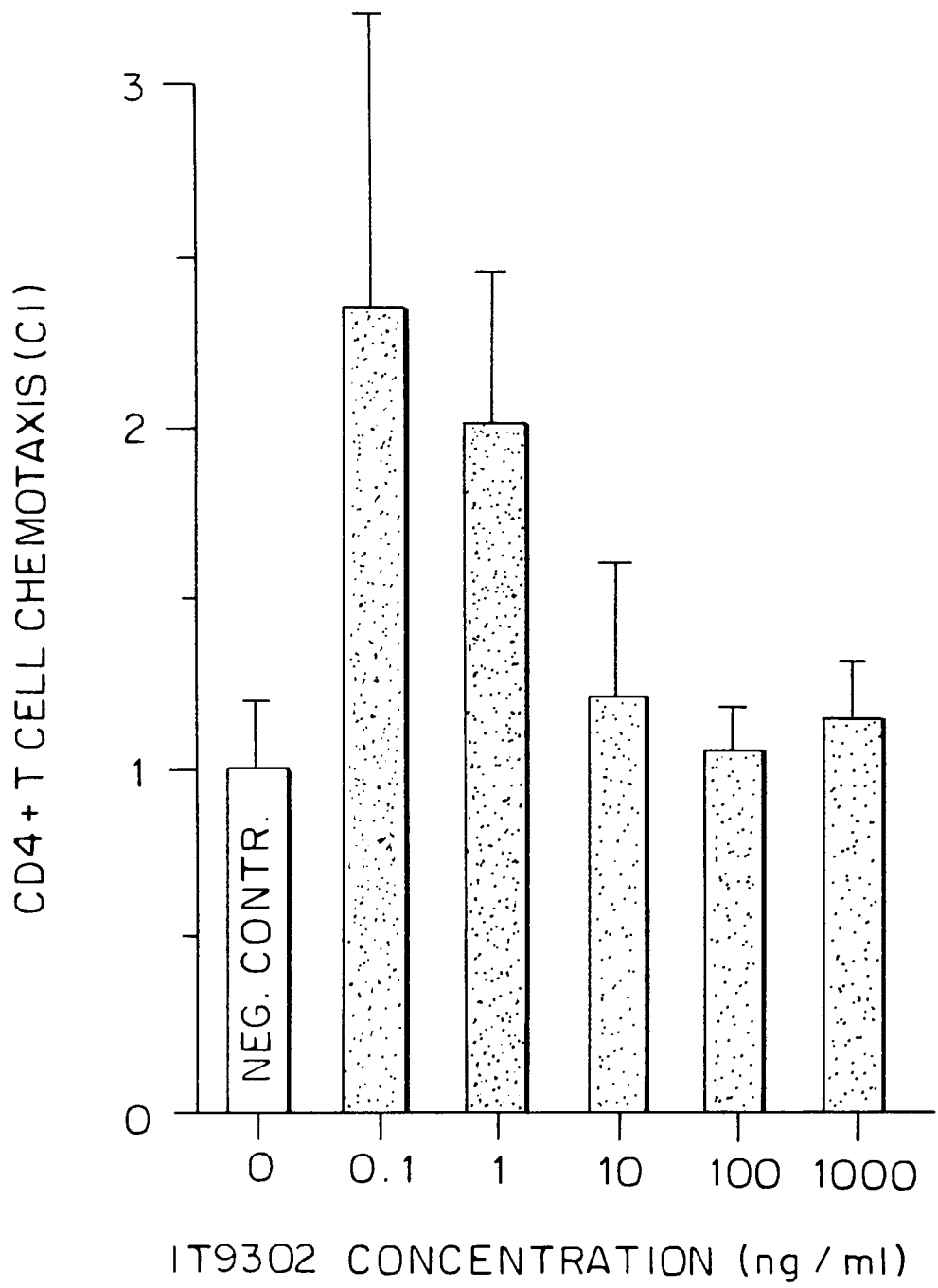
FIG. 9 illustrates the suppression of IL-8 activity by IT9302. The drawing shows the effect of IT9302 on IL-8 (10 ng/ml) mediated chemotaxis.

The experiment was carried out as described in "Leukocyte chemotaxis assay". As shown in FIG. 9, IT9302, in a dose-dependent manner and added to a suspension of human CD4+ T lymphocytes, inhibits the response of the CD4+ T cells towards IL-8.

Example 7

IT9302 Suppresses the Chemotactic Response of Human Monocytes Towards MCAF/MCP-1

Figure 10:
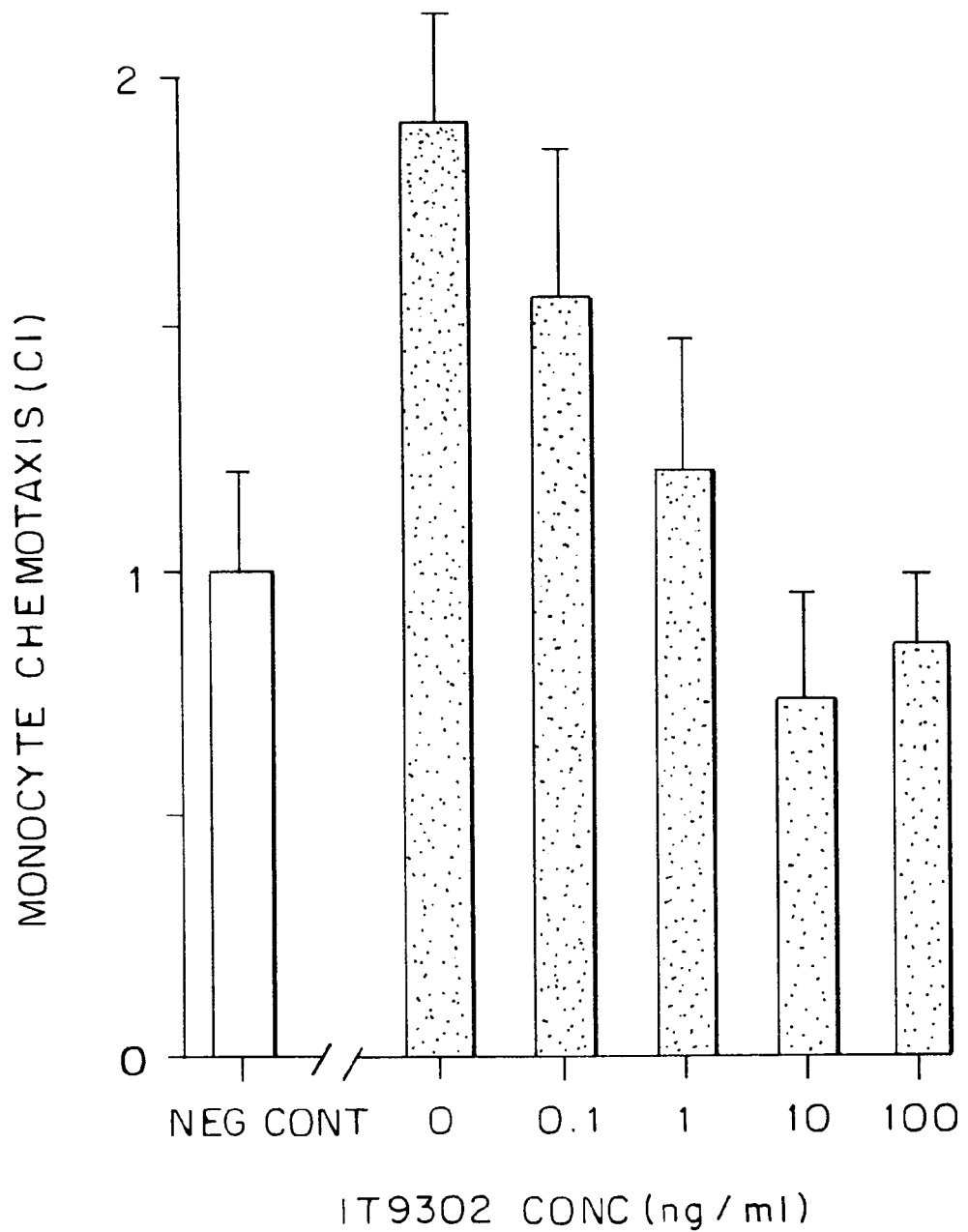
FIG. 10 is a diagram showing that IT9302 inhibits MCAF/MCP-1 induced monocyte chemotaxis.

The experiment was carried out as described in "Monocyte chemotaxis". As shown in FIG. 10, IT9302, in a dose-dependent manner and added to a suspension of human monocytes, inhibits the chemotactic response of the monocytes towards MCAF/MCP-1.

Example 8

IT9302 Does Not Inhibit Class II MHC Molecule Expression on Human Monocytes

The experiment was carried out as described in Materials and Methods and show that rhIL-10 inhibits class II MHC expression but IT9302 does not, as shown below in Table 4.

TABLE 4

| Stimulation | Number of rosetting monocytes |
|---|---|
| 0 | $12.0 \pm 1.0 \times 10^4$ |
| 100 ng/ml rhIL-10 | $4.6 \pm 1.4 \times 10^4$ |
| 1 µg/ml IT9302 | $11.0 \pm 3.0 \times 10^4$ |
| 100 ng/ml IT9302 | $14.4 \pm 2.4 \times 10^4$ |
| 10 ng/ml IT9302 | $11.2 \pm 3.2 \times 10^4$ |

Discussion Related to the Experiments

The present data demonstrate a dose-dependent inhibitory effect of the synthetic nonapeptide, IT9302, on processes which reflect pro-inflammatory activity, including IL-8 production and monocyte and/or T cell migration. Thus, IT9302 was able to suppress the spontaneous production of IL-8 by human monocytes cultured overnight. This could be explained by a direct inhibitory effect on IL-8 mRNA production and/or subsequent protein production and or release. Another mechanism could be explained by the fact that monocytes cultured in vitro will express and produce IL-1, which then in turn induces the production of IL-8. This is supported by the fact that it has been demonstrated that IT9302 potently induces the production of IRAP from monocytes. IT9302 may therefore also inhibit spontaneous IL-8 production by interfering with the activity of IL-1. The observed IRAP induction by IT9302 appears to induce a biologically active IRAP, since IT9302 added to the cultures counteracts IL-1-induced IL-8 production, but only when added at least 16 hours before adding IL-1 to the cultures. This could mean that IT9302 inhibits IL-1-induced IL-8 production by inducing the production of IRAP, which then in turn blocks the activity of IL-1 through its receptor. If IT9302 directly inhibited IL-8 production, it would have been expected that-addition of IT9302 to the cultures 1 hour before adding IL-1 should inhibit IL-8 production, which was not the case (data not shown). Therefore, the observed inhibition of IL-8 production of IT9302 is likely to be due to an induction of IRAP production rather than a direct inhibition of IL-8 production. These functions of IT9302 can also be found for hIL-10 indicating that IT9302 possesses IL-10-like activities. IT9302 also mimics IL-10 activity by suppressing the ability of CD4+ T cells to migrate as a response to IL-8. Since IL-8 is related to many different states of inflammation and since CD4+ T cells appear early in the infiltrate of T cell-mediated immune inflammation such as allergy of the skin, this feature may prove to have significant therapeutic value for the control of T cell-mediated immune inflammation.

The demonstrated CD8+ T cell chemotactic activity of IT9302 is also parallel to that of IL-10, and IT9302 may thus activate T cell populations with suppressor activity contributing to the ending of T cell-mediated immune inflammation. Therefore IT9302 according to the examples which are demonstrated above, possesses therapeutic value in diseases where IL-10 and/or IRAP may also have therapeutic value. Additionally, IT9302 may have therapeutic value in diseases where IL-8 and/or MCAF and/or IL-1 are believed to have pathogenetic roles.

Example 9
IT9302 and IL-10 Induce the Production of IL-4 in CD4+ T Lymphocytes Background Like IL-10, IL-4 is a product of CD4+ T cells of $T_H2$ type. It was observed that recombinant human IL-10 induces the production of IL-4 by cultured human CD4+ T cells. This means that IL-10, in addition to its own immunosuppressive functions, also induces the production of another immunosuppressive cytokine, IL-4. It was therefore tested whether IT9302 also induces the production of IL-4 by CD4+ T cells.

Thus, CD4+ T cells, purified as described in "Methods for T cell chemotaxis", and cultured as described in the section "Determination of IL-4 production by CD4+ T lymphocytes", were stimulated for 3 days with IT9302 (10 ng/ml) or IL-10 (100 ng/ml). Cytosolic fractions were collected and analyzed for their IL-4 content using Western blotting (FIG. 11) and a goat anti-human IL-4 polyclonal antibody.

Figure 11:
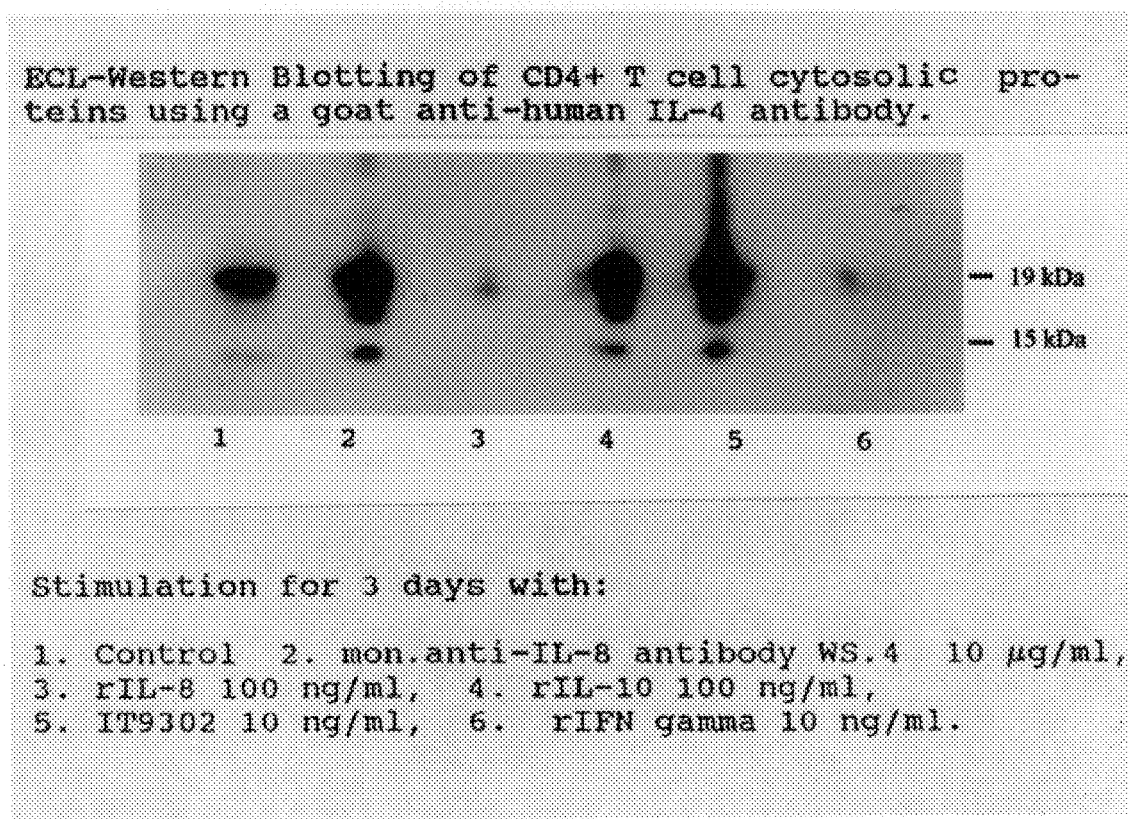
FIG. 11 shows IL-4 production in CD4+ T cell cytosolic fractions by ECL-Western Blotting.

As demonstrated in FIG. 11, it was observed that IL-10 as well as IT9302 induce the production of IL-4 by cultured normal human CD4+ T cells.

Example 10
IT9302 Inhibits the Production of TNF-α During a Mixed Leukocyte Reaction (MLR)

It has been demonstrated that the mixed leukocyte reaction is partly dependent on the production of TNF-α during the reaction. It has been shown that IT9302 does not significantly reduce the MLR, but it was found that there is a significant reduction in the production of TNF-α during the MLR.

Thus, MLR was performed by purifying human leukocytes and then culturing 1 million cells/ml from allogeneic donors for 4 days. Before establishing the cultures, one group of cells was irradiated for 2 minutes using beta irradiation. Cytosolic protein fractions were purified as described in the section "Determination of IL-4 production by CD4+ T lymphocytes", and Western blotting was performed using a rabbit anti-human TNF-α antibody.

As demonstrated in FIG. 12, a significant reduction in the production of TNF-α was observed during a human mixed leukocyte reaction.

Example 11
The Modulation of the LPS Induced Shock and Leukopenia in Swine Using IT9302

Since it was found that IT9302 modulates cytokine production, including TNF-α and IL-8, and supported by the published sequence of porcine IL-10 (Blancho et al., 1995) (see FIG. 2 for homology to the COOH-terminal peptide), it was tested whether IT9302 was able to modulate the course of LPS induced leukopenia in swine (FIG. 13).

In a preliminary experiment, it was tested how the intravenous injection of IT9302 0.1 mg/kg modulated the effect of intravenous injection of 2 µg/kg LPS in swine (N=3). IT9302 was injected 30 minutes before injection of LPS, and blood samples were drawn as described in FIG. 13. Total leukocyte count as well as differential cell count were determined, and the total number of neutrophilic leukocytes was calculated on the basis of these results.

As demonstrated, it was observed that injection of LPS caused a transient leukopenia. Injection of IT9302, however, prevented leukopenia as demonstrated in the figure.

Example 12
Antibody Against the Synthetic Polypeptide IT9302

Synthetic polypeptide IT9302 was purchased from Kem-En-Tec A/S, Copenhagen, Denmark, with higher purity than 95%. This polypeptide was also conjugated to Keyhole Limpet Hemocyanin (KLH) by the producer. The soluble IT9302/KLH is more immunogenic than the polypeptide alone, and it may also be used as control protein for ELISA or Western Blotting.

Immunization of Rabbits

250 µg of IT9302 coupled to KLH, and as an emulsion with complete Freund's adjuvant, is used for intradermal or subcutaneous injections. The injections are repeated 4 times with two-week intervals and the rabbits are bled 8 and 12 days thereafter. Later booster injections of 250 μg of IT9302/KLH in incomplete Freund's adjuvant are administered with one-month intervals using subcutaneous injections. The formation of IT9302 antibody is tested by dot-blot immunoassay or Western Blotting.

References

1. Bendtzen K. Lymphokines in inflammation. Inflammation Basic Mechanisms Tissue Injuring Principles and Clinical Models (P Venge & A Lindbom eds) 1985; Almqvist & Wiksell International. Stockholm: 187–217.
2. Bendtzen K. Interleukin-1, Interleukin-6, and tumor necrosis factor in infection, inflammation and immunity. Immunol Lett 1988;19:183–192.
3. Larsen C. G. Leukocyte activating and chemotactic cytokines in cell-mediated immune reactions of the human skin. Acta Dermatovenerol. 1991; Suppl. 160:1–48
4. Fiorentino D. F., M. W. Bond, and T. R. Mosmann. 1989. Two types of mouse helper T cell. IV. Th2 clones secrete a factor that inhibits cytokine production by Th1 clones. J. Exp. Med., 170:2081.
5. Viera P., R. de Wall-Malefyt, M. -N. Dang, K. E. Johnson, R. Kastelein, D. F. Fiorentiono, J. E. de Vries, M. -G. Roncarolo, T. R. Mosmann, and K. W. Moore. 1991. Isolation and expression of human cytokine synthesis inhibitory factor (CSIF/IL-10) cDNA clones: homology to Epstein-Barr virus open reading frame BCRFI. Proc. Natl. Acad. Sci. (U.S.A.), 88:1172.
6. Moore, K. W., O'Garra A., de Waal Malefyt R., Vieira, Mosmann T. R. 1993. Interleukin-10, Annu Rev. Immunol, 11:165–90.
7. Kim, J. M., Brannan, C. I. Copeland N. G., Jenkins, N. A., Khan, T. A., Moore, K. W. 1992. Structure of the mouse interleukin-10 gene and chromosomal localization of the mouse and human genes. J. Immunol 148:3618–23.
8. Carter, D. B., Deibel, M. R -Jr, Dunn, C. J. et al. 1990. Purification, cloning, expression and biological characterization of an interleukin-1 receptor antagonist protein. NATURE 344:633–638.
9. Hannum, C. H., Wilcox, C. J., Arend, W. P. et al. 1990. Interleukin-1 receptor antagonist activity of a human interleukin-1 inhibitor. Nature 343:336–40.
10. Firestein, G. S., Boyle, D. L., Yu, C., et al. 1994. Synovial interleukin-1 receptor antagonist and interleukin-1 balance in rheumatoid arthritis. Arthritis Rheum 37:644–652.
11. Fisher, C. J. -Jr.,Slotman, G. J., Opal, S. M., Pribble, J. P. et al. 1994. Initial evaluation of recombinant interleukin-1 receptor antagonist in the treatment of sepsis syndrome: a randomized, open-label, placebo-controlled multicenter trial. The IL-1RA Sepsis Syndrome Study Group. Crit-Care-Med. 22:12–21.
12. de Waal-Malefyt, R., Haanen J., Spits, H., et al. 1991. IL-10 and viral IL-10 strongly reduce antigen-specific human T cell proliferation by diminishing the antigen-presenting capacity of monocytes via down-regulation of class II MHC expression. J. Exp. Med. 174:915–24.
13. Gazzinelli, R. T., Oswald, I. P., James, S. L., Sher, A., 1992. IL-10 inhibits parasite killing and nitric oxide production by IFN-/-activated macrophages. J. Immunol. 148:1792–96.
14. Jinquan, T., Larsen, C. G., Gesser, B., Matsushima, K., Thestrup-Pedersen, K. 1993. Human IL-10 is a chemoattractant for CD8+ T lymphocytes and an inhibitor of IL-8-induced CD4+ T lymphocyte Migration. Journal of Immunology, 151:4545–4551.
15. Rousset F., E. Garcia, T. Defrance, C. Peronne, D. -H. Hsu, R. Kastelein, K. W. Moore, and J. Banchereau. 1992. IL-10 is a potent growth and differentiation factor for activated human B lymphocytes. Proc. Natl. Acad. Sci. U.S.A., 175:671.
16. Howard, M., O'Garra, A., Ishida, H., de Waal Malefyt, R., de Vries, J. 1992. Biological properties of Interleukin-10. J. Clin. Immunol 12:239–47.
17. Kuhn, R., Lohler, J., Rennick, D., Rajewsky, K., Muller, W. 1993. Interleukin-10-deficient mice develop chronic enterocolitis. Cell 75: 263–74.
18. Sher, A., Fiorentino, D. F., Caspar, P., Pearce, E., Mosmann, T. 1991. Production of IL-10 by CD4+ lymphocytes correlates with down-regulation of Th1 cytokine synthesis in helminth infection. J. Immunol. 147:2713–16.
19. Clerici, M., Shearer, G. M. 1993 Immunology Today. 14:107–111.
20. Bry, K., Lappalainen, U. 1994. Interleukin-4 and transforming growth factor-beta 1 modulate the production of interleukin-1 receptor antagonist and prostaglandin E2 by decidual cells. Am-J-obstet-Gynecol 170 (4): 1194–1198
21. Firestein, G., S., Boyle, D. L., Yu, C., Paine, M. M., Whisenand, T. D., Zvaifler, N. J., Arend, W. P. 1994. Synovial interleukin-1 receptor antagonist and interleukin 1 balance in rheumatoid arthritis. Arthritisrhuem, 37/5: 644–652
22. Roberge, C. J., De-Medicis, R., Dayer, J. M., Rola-Pleszcyczynski, M., Naccahe, P. H., Poubelle, P. E. 1994. Crystal-induced neutrophil activation: V. Differential production of biologically active IL-1 receptor antagonist. J. Immunol 152/11: 5485–5494
23. McCall, R. D., Haskill, S., Zimmermann, E. M., Lund, P. K., Thompson, R. C., Sartor, R. B. 1994. Tissue interleukin 1 and interkeukin-1 receptor antagonist expression in entercolitis in resistant and susceptible rats. Gastroenterology (4): 960–72
25. Kimble, R. B., Vannice, J. L, Bloedow, D. C., Thompson, R. C., Hopfer, W., Kung, V. T., Brownfield, C., Pacifici, R. 1994. Interleukin-1 receptor antagonist decreases bone loss and bone resorption in ovariectomized rats. J. Clin Invest. 93/5: 1959–1967
26. Kline, J. N., Geist, L. J., Monick, M. M., Stinski, M. F., Hunninghake, G. W., 1994. J. Immunol. 152 (5): 2351–7
27. Tompkins, R. G. 1994. Human recombinant interleukin-1 receptor antagonist in the treatment of sepsis syndrome (editorial; comment). Crit-Care-Med. 22 (1): 3, 22 (1):12–21
28. Everaerdt, B., Brouckaert, P., Fiers, W. 1994. Recombination IL-1 receptor antagonist protects against TNF-induced lethality in mice. J. Immunol. 152/10: 5041–5049
29. Fischer, C. J. Jr., Slotman, G. J., Opal, S. M., Pribble, J. P., Bone, R. C., Emmanuel, G., Ng, D., Bloedow, D. C., Catalano, M. A. 1994. Initial evalutaion of human recombination interleukin-1 receptor antagonist in the treatment of sepsis syndrome: a randomized, open-label, placebo-controlled multicenter trial. The IL-1RA Sepsis Syndrome Study Group (see comments). Crit-Care-Med. 22(1): 12–21, 22(1): 3
30. Gomez-Reino-Carnoto, J. J. 1994. New terapies in rheumatoid arthritis. Med-Clin 543–545.
32. Nishihara, T., Ohsaki, Y., Ueda, N., Saito, N., Mundy, G. R. 1994. Mouse interleukin-1 receptor antagonist induced by actinobacillus actinomycetemcomitans lipopolysaccharide blocks the effects of interleukin-1 om bone resorption and osteoclast-like cell formation. Infect-Immun. 62(2): 390–7

33. Simon, C., Frances, A., Piquette, G. N., el-Danasouri, I., Zurawski, G., Dang, W., Polan, M. L. 1994. Embryonic implantation in mice is blocked by interleukin-1 receptor antagonist (see comments). Endocrinology. 134(2): 521–8, 134(2): 519–20
34. Baergen, R., Benirschke, K., Ulich, T. R., 1994. Cytokine expression in the placenta. The role of interleukin 1 and interleukin 1 receptor antagonist expression in chorioamnionitis and parturition. Arch-Pathol-Lab-Med. 118(1): 52–5
35. Tang, W. W., Feng, L., Vannice, J. L., Wilson, C. B. 1994. Interleukin-1 receptor antagonist ameliorates experimental antiglomerular basement membrane antibody-associated flomeulonephritis. J. Clin-Invest. 93(1): 279–9.
36. Cassatella, M. A., Meda, L., Gasperini, S., Calzetti, F., Bonara, S. 1994.
37. Interleukin 10 (IL-10) upregulates IL-1 receptor antagonist production from lipopolysaccharide-stimulated human polymorphonuclear leukocytes by delaying mRNA degradation. J. Exp-Med. 179/5: 1695–1699
38. Mancini, R., Bendetti, A., Jezequel, A. M. 1994. An interleukin-1 receptor antagonist decreases fibrosis induced by dimethylnitrorsamine in rat liver. Virchows-Arch. 424/1: 25–31
39. Lukacs, N. W., Kunkel, S. L., Burdick, M. D., Lincoln, P. M., Strieter, R. M. 1993.
40. Interleukin-1 receptor antagonist blocks chemokine production in the mixed lymphocyte reaction. Blood. 82(12): 3668–74
41. Bandara, G., Mueller, G. M., Galea-Lauri, J., Tindal, M. H., Georgescu, H. I., Suchanek, M. K., Hung, G. L., Gloriso, J. C., Robbins, P. D., Evans, C. H. 1993.
42. Intraarticular expression of biologically active interleukin 1-receptor-antagonist protein by ex vivo transfer. Proc-Natl-Acad-Sci-U.S.A. 90(22): 10764–8
43. Dinarello, C. A. 1994. Anti-interleukin-1 strategies in the treatment of the septic shock syndrome. Can-J-infect-Dis. 5(suppl. A): 9A–16A
44. Oelmann, E., Topp, M. S., Reufi, B., Papadimitriiou, C., Koeningsmann, M., Oberberg, D., Thiel, E., Berdel, W. E. 1994. Int-J-Oncol. 4/3: 555–558
45. Estrov, Z. 1993. Interruption of autocrine and paracrine growth-stimolatory mechaisms: a new therapeutic stratefy for chronic myelogenous leukemia. Semin-Hematol. 30(3 suppl 3): 35–6
46. Wooley, P. H., Whalen, J. D., Chapman, D.L., Berger, A. E., Richard, K. A., Aspar, D. G., Staite, N. D. 1993. The effect of an interleukin-1 receptor antagonist protein on type II collagen-induced arthritis and antigen-induced arthritis in mice. Arthritis Rheum. 36 (9): 1305–1314
47. Peterson, C. M., Hales, H. A., Hatasaka, H. H., Mitchell, M. D., Rittenhouse, L., Jones, K. P. 1993. Interleukin-1 beta (IL-1 beta) modulates prostaglandin production and the natural IL-1 receptor antagonist inhibits ovulation in the optimally stimulated rat ovarian perfusion model. Endocrinology 133 (5): 2301–2306
48. Estrov, Z., Kurzrock, R., Talpaz, M. 1993. Role of interleukin-1 inhibitory molecules in therapy of acute and chronic myelogenous leukemia. Leuk. Lymphoma 10 (6): 407–418
49. Chensue, S. W., Bienkowski, M., Eessalu, T. E., Warmington, K. S., Hershey, S. D., Lukacs, N. W., Kunkel, S. L. 1993. nous IL-1 receptor antagonist protein (IRAP) regulates schistosome egg granuloma formation and the regional lymphoid response. J. Immunol. 151 (7): 3654–3662
50. Bowyer, J. F., Davies, D. L., Schmued, L., Broening, H. W., Newport, G. D., Slikker, W Jr., Holson, R. R. 1994. Further studies of the role f hyperthermia in methamphetamine neurotoxicity. J. Pharmacol. Exp. Ther. 268/3:1571–1580
51. Cole, O. F., Sullivan, M. H. F., Elder, M. G. 1993. The 'interleukin-1 receptor antagonist' is a partial agonist of prostaglandin synthesis by human decidual cells. Prostaglandins 46/6: 493–498
52. Jenkins, J. K., Arend, W. P. 1993. Interleukin 1 receptor antagonist production in human monocytes is induced by IL-1alpha, IL-3, and IL-4 and GM-CSF. Cytokine 5/5: 407–415
53. Coceani, F., Lees, J., Redford, J., Bishai, I. 1992. Interleukin-1 receptor antagonist: effectiveness against interleukin-1 fever. Can. J. Pharmacol. 70 (12): 1590–1596
54. Schiro, R., Longoni, D., Rossi, V., Maglia, O., Doni, A., Arsura, M., Carrara, G., Masera, G., Vannier, E., Dinarello, C. A., Rambaldi, A., Biondi, A. 1994. Suppression of juvenile chronic myelogenous leukemia colony growth by interleukin-1 receptor antagonist. Blood 83/2:460–465
55. Watson, M. L., Smith, D., Bourne, A. D., Thompson, R. C., Westwick, J. 1993. Cytokines contribute to airway dysfunction hyperreactivity, pulmonary eosinophil accumulation and tumor necrosis factor generation by pretreatment with an interleukin-1 receptor antagonist. Am. J. Respir. Cell Mol. Biol. 8 (4): 365–369
56. Abhyankar, S., Gilliland, D. G., Ferrara, J. L. M. 1993. Interleukin-1 is a critical effector molecule during cytokine dysregulation in graft-versus-host disease to minor histocompatibility antigens. Transplantation 56/6:1518–1523
57. Lan, H. Y., Nikolic Paterson, D. J., Zarama, M., Vannice, J. L., Atkins, R. C. 1993. Suppression of experimental crescentic glomerulonephritis by the interleukin-1 receptor antagonist. Kidney Int. 43 (2): 479–485
58. Herve, P. 1993. Prevention and treatment of acute GvHD—New modalities. Nouv. Rev. Fr. Hematol. 35/3: 295–297
59. Conti, P., Panara, M. R., Barbacane, R. C., Placido, F. C., Bongrazio, M., Reale, M., Dempsey, R. A., Fiore, S. 1992. Blocking the interleukin-1 receptor inhibits leukotriene B4 and prostaglandin E2 generation in human monocyte cultures. Cell Immunol. 145 (1): 199–209
60. Kristensen, M., Deleuran, B., Eedy, D. J., Feldmann, M., Breathnach, S. M., Brennan, F. M. 1992. Distribution of interleukin-1 receptor antagonist protein (IRAP), interleukin-1 receptor, and interleukin-1 alpha in normal and psoriatic skin, Decreased expression of IRAP in psoriatic lesional epidermis. Br. J. Dermatol. 127 (4): 305–311
61. Romero, R., Sepulveda, W., Mazor, M., Brandt, F., Cotton, D. B., Dinarello, C. A:, Mitchell, M. D. 1992. The natural interleukin-1 receptor antagonist in term and preterm parturition. Am. J. Obstet. Gynecol. 167 (4 Pt 1): 863–872
62. Dinarello, C. A. 1992. Reduction of inflammation by decreasing production of interleukin-1 or by specific receptor antagonism. Int. J. Tissue. React. 14 (2): 65–75
63. Conti, P., Panara, M. R., Barbacane, R. C., Bongrazio, M:, Dempsey, R. A., Reale, M. 1993. Human recombinant IL.1 receptor antagonist (IL-1Ra) inhibits leukotriene B4 generation from human monocyte suspensions stimulated by lipopolysaccharide (LPS). Clin. Exp. Immunol. 91/3: 526–531

64. DeForge, L. E., Tracey, D. E., Kenney, J. S., Remick, D. G. 1992. Interleukin-1 receptor antagonist protein inhibits interleukin-8 expression in lipopolysaccharide-stimulated human whole blood. Am. J. Pathol. 140 (5): 1045–1054
65. Porat, R., Poutsiaka, D. D., Miller, L. C., Granowitz, E. V., Dinarello, C. A. 1992. Interleukin-1 (IL-1) receptor blockade reduces endotoxin and Borrealia burgdorferi-stimulated IL-8 synthesis in human monoclear cells. Faseb. J. 6 (7): 2482–2486
66. Boermeester, M. A., van Leeuwen, P. A. M., Schneider, A. J., Houdijk, A. P. J., Ferwerda, C. C., Wesdorp, R. I. C. 1993. Interleukin-1 receptor antagonist: A new therapeutic agent in the treatment of septic syndrome. Ned. Tijdschr. Geneesks. 137/7: 337–342
67. Smith, R. J., Chin, J. E., Sam, L. M., Justen, J. M. 1991. Biologic effects of an interleukin-1 receptor antagonist protein on interleukin-1-stimulated cartilage erosion and chondrocyte responsiveness. Arthsitis Rheum. 34 (1):78–83
68. Conti, P. Barbacane, R. C., Panara, M. R., Reale, M., Placido, F. C., Eridas, S., Bongrazio, M., Dempsey, R. A. 1992. Human recombinant interleukin-1 receptor antagonist (hrIL-1ra) enhances the stimulatory effect of interleukin-2 on natural killer cell activity against MOLT-4 target cells. Int. J. Immunopharm. 14/6: 987–993
69. Selig, W., Tocker, J. 1992. Effect of interleukin-1 receptor antagonist on antigen-induced pulmonary responses in guinea pigs. Eur. J. Pharmacol. 213/3: 331–336
70. McCarthy, P. L. Jr., Abhyankar, S., Neben, S., Newman, G., Sieff, C., Thompson, R. C., Burakoff, S. J., Ferrara, J. L. M. 1991. Inhibition of interleukin-1 by an interleukin-1 receptor antagonist prevents graft-versus-host diseases-.Blood 78/8: 1915–1918
71. Estrov, Z, Kurzrock, R., Wetzler, M., Kantarjian, H., Blake, M., Harris, D., Gutterman, J. U., Talpaz, M. 1991. Suppression of chronic myelongenous leukemia colony growth by interleukin-1 (IL-1) receptor antagonist and soluble IL-1 receptors: A novel application for inhibitors of IL-1 activity. Blood 78/6: 1476–1484
72. Thomas, T. K., Will, P. C., Srivastava, A., Wilson, C. L., Harbison, M., Little, J., Chesonis, R. S., Pignatello, M., Schmolze, D., Symington, J., Kilin, P. L., Thompson, R. C. 1991. Evaluation of an interleukin-1 receptor antagonist in the rat acetic acid-induced colitis model. Agents Actions 34/1–2: 187–190
73. Carter, D. B., Deibel, M. R. Jr., Dunn, C. J., Tomich, C. S. C., Laborde, A. L., Slightom, J. L., Berger, A. E., Bienkowski, M. J., Sun, F. F., McEwan, R. N., Harris, P. K. W., Yem, A. W., Waszak, G. A., Chosay, J. G., Sieu, L. C., Hardee, M. M., Zurcher Neely, H. A., Reardon, I. M., Heinrikson, R. L. et al. 1990. Purification, cloning expression and biological characterization of an interleukin-1 receptor antagonist protein. Nature 344/6267:633–638
74. Larsen C. G, Anderson A. O, Apella E., Oppenheim J. J., Matsushima K., 1989. Science 243:1464;
75. Larsen C. G., Jinquan T., Deleurant B., Thestrup-Pedersen K. 1993, IL-10 is a potent regulator of the chemotactic response of mononuclear cells, but not of granulocytes. J. Invest. Dermatol. Vol 100, No 6
76. Sankoff and Kruskal in chapter 1 of "Time Warps, String Edits, and Macromolecules: The Theory and Practice of Sequence Comparison" (Addison-Wesley, Reading, Mass. 1983).
77. Berzofsky, Science 229, (1985) 932–940
78. Bowie et al., Science 247, (1990) 1306–1310
79. Wasserman et al., J. Immunol. 87, 1961, 290–295
80. Levine et al., Methods in Enzymology 11, 1967, 928–936
81. Lewis et al., Biochemistry 22, 1983, 948–954
82. Rene de Waal Maletyt, John Abrahams, Bruce Bennet, Carl G. Figdor and Jan E. de Vries (1991), Interleukin 10 (IL-10) Inhibits Cytokine Synthesis by Human Monocytes: An Autoregulatory Role of IL-10 Produced by Monocytes. J. Exp. Med. 174, 1209–1220
83. Szoka et al., Ann. Rev. Biophys. Bioeng. 9, 1980, 467
84. U.S. Pat. No. 4,235,871
85. U.S. Pat. No. 4,501,728
86. U.S. Pat. No. 4,837,028.
87. Walter H. Gotlieb, John S. Abrams, Joanna M. Watson, Thierry J. Velu, Jonathan S. Berek, Otoniel Martinez-Meza (1992), Presence of interleukin 10 (IL-10) in the ascites of patients with ovarian and other intra-abdominal cancers. Cytokine 4, No. 5, 385–390
88. Blancho G., P. Gianello, Sh. Germana, M. Baetscher, D. H. Sachs and Chr. LeGuern (1995), Molecular identification of porcine interleukin 10: Regulation of expression in kidney allograf model. Proc. Natl. Acad. Sci. USA 92, 2800–2804

What is claimed is:

1. A substance which is (I) a polypeptide amounting to 9 to 20 amino acids, said polypeptide comprising the following sequence:

$X_1$-$X_2$-$X_3$-Thr-$X_4$-Lys-$X_5$-Arg-$X_6$    (SEQ ID NO:22), wherein $X_1$ is Ala or Gly, $X_2$ is Tyr or Phe, $X_3$, $X_4$ and $X_5$ are independently selected from the group consisting of Met, Ile, Leu and Val; and $X_6$ is selected from the group consisting of Asn, Asp, Gln and Glu, and which has one or more of the following properties:

(a) induces inhibition of spontaneous IL-8 production by human monocytes, (b) induces inhibition of IL-1β induced IL-8 production by human peripheral blood mononuclear cells, (c) induces production of interleukin-1 receptor antagonistic protein (IRAP) by human monocytes, (d) induces chemotactic migration of CD8$^+$ human T lymphocytes in vitro, (e) desensitizes human CD8$^+$ T cells resulting in an unresponsiveness towards recombinant human IL-10 (rhIL-10), (f) suppresses the chemotactic response of CD4$^+$ human T lymphocytes towards IL-8, (g) suppresses the chemotactic response of human monocytes towards MCAF/MCP-1, (h) induces the production of IL-4 by cultured normal human CD4+ T cells, or (i) reduces the TNFA production in human mixed leukocyte reaction, or, (II) a salt, ester or a conjugate of said polypeptide, but said conjugate is not IL-10 or a fragment of IL-10 which amounts to more than 20 amino acids of IL-10.

2. A substance according to claim 1, wherein $X_1$ is Ala.
3. A substance according to claim 1, wherein $X_1$ is Gly.
4. A substance according to claim 1, wherein $X_2$ is Tyr.
5. A substance according to claim 1, wherein $X_2$ is Phe.
6. A substance according to claim 1, wherein $X_3$ is Met.
7. A substance according to claim 1, wherein $X_3$ is Ile.
8. A substance according to clalm 1, wherein $X_3$ is Leu.
9. A substance according to claim 1, wherein $X_3$ is Val.
10. A substance according to claim 1, wherein $X_4$ is Met.
11. A substance according to claim 1, wherein $X_4$ is Ile.
12. A substance according to claim 1, wherein $X_4$ is Leu.
13. A substance according to claim 1, wherein $X_4$ is Val.
14. A substance according to claim 1, wherein $X_5$ is Met.
15. A substance according to claim 1, wherein $X_5$ is Ile.
16. A substance according to claim 1, wherein $X_5$ is Leu.
17. A substance according to claim 1, wherein $X_5$ is Val.
18. A substance according to claim 1, wherein $X_6$ is Asp.
19. A substance according to claim 1, wherein $X_6$ is Gln.
20. A substance according to claim 1, wherein $X_6$ is Glu.
21. A substance according to claim 1, wherein $X_6$ is Asn.
22. A substance according to claim 1, which is a polypeptide in substantially pure form.
23. A substance according to claim 1 comprising at least 12 amino acids.
24. A substance according to claim 1 comprising at least 15 amino acids.
25. A substance according to claim 1 which is 11 amino acids long.
26. A substance according to claim 1 which is 10 amino acids long.
27. A substance which is a polypeptide as defined in claim 1 or is a salt or ester of said polypeptide.
28. A substance according to claim 1, wherein the substance is a conjugate which is a sugar conjugate or a polyethylene glycol conjugate of said polypeptide.
29. A composition comprising the substance according to claim 1 and a liposome, the substance being encapsulated in said liposome.
30. The substance of claim 1, which is said polypeptide.
31. The substance of claim 1, which is a polypeptide which amounts in total from 6 to 10 amino acids.
32. The substance of claim 1 which is a polypeptide which amounts in total to 9 amino acids.
33. The substance of claim 1 where said polypeptide amounts to 9 to 20 amino acids and comprises the amino acid sequence Ala-Tyr-Met-Thr-Met-Lys-Ile-Arg-Asn (SEQ ID NO:1).
34. A pharmaceutical composition comprising a substance according to claim 3.
35. A method of
(a) inducing inhibition of spontaneous IL-8 production by human monocytes,
(b) inducing inhibition of IL-1β induced IL-8 production by human peripheral blood mononuclear cells,
(c) inducing production of interleukin-1 receptor antagonistic protein (IRAP) by human monocytes,
(d) inducing chemotactic migration of CD8+ human T lymphocytes,
(e) desensitizing human CD8+ T cells resulting in an unresponsiveness towards recombinant human IL-10 (rhIL-10),
(f) suppressing the chemotactic response of CD4+ human T lymphocytes towards IL-8, (g) suppressing the chemotactic response of human monocytes towards MCAF/MCP-1,
(h) inducing the production of IL-4 by human CD4+ T cells, or
(i) reducing TNFα production in human leukocytes,
in a patient in need of such treatment, the method comprising administering to said patient an amount of a substance according to claim 1 in an amount effective to therapeutically or prophylactically achieve such induction, desensitization, suppression, or reduction.

36. The method of claim 35 where said substance is said polypeptide, or is a salt, or ester of said polypeptide.
37. The method of claim 35 where said substance is said polypeptide.
38. The method of claim 35 where said substance is a polypeptide having the formula Ala-Tyr-Met-Thr-Met-Lys-Ile-Arg-Asn  (SEQ ID NO:1).

39. The method of claim 35, wherein said patient is afflicted with a disorder selected from the group consisting of pre-term labour caused by infection, rheumatoid arthritis, Lyme's arthritis, gout, sepsis syndrome, hyperthermia, ulcerative colitis, enterocolitis, osteoporosis, cytomegalovirus, periodontal disease, glomerulonephritis, chronic non-infectious inflammation of the lung, sarcoidosis, smoker's lung, granuloma formation, fibrosis of the liver, fibrosis of the lung, transplant rejection, graft vs. host disease, chronic myeloid leukemia, acute myeloid leukemia, neoplastic diseases, asthma bronchiale, type I insulin dependent diabetes mellitus, arteriosclerosis, atherosclerosis, psoriasis, chronic B lymphocyte leukaemia, common variable immunodeficiency, disseminated intravascular coagulation, systemic sclerosis, encephalomyelitis, lung inflammation, hyper IgE syndrome, cancer metastasis, cancer growth, adoptive immune therapy, acquired respiratory distress syndrome, sepsis, reperfiision syndrome, post-surgical inflammation, organ transplantation, and alopecia.

40. An isolated nucleotide sequence encoding the substance according to claim 1, wherein said substance is said polypeptide.
41. A vector which comprises the nucleotide sequence of claim 40.
42. The vector of claim 41 where said nucleotide sequence encodes Ala-Tyr-Met-Thr-Met-Lys-Ile-Arg-Asn (SEQ ID NO:1).
43. A polypeptide consisting of the amino acid sequence Ala-Tyr-Met-Thr-Met-Lys-Ile-Arg-Asn (SEO ID NO:1).
44. A polypeptide selected from the group consisting of
Ala-Tyr-Met-Thr-Ile-Lys-Met-Arg-Asn (SEQ ID NO:2),
Ala-Phe-Met-Thr-Leu-Lys-Leu-Arg-Asn (SEQ ID NO:3),
Ala-Tyr-Met-Thr-Met-Lys-Val-Arg-Glu (SEQ ID NO:4),
Gly-Tyr-Met-Thr-Met-Lys-Ile-Arg-Asp (SEQ ID NO:5),
Ala-Phe-Met-Thr-Met-Lys-Ile-Arg-Asp (SEQ ID NO:6),
Ala-Tyr-Ile-Thr-Met-Lye-Ile-Arg-Asp (SEQ ID NO:7),
Ala-Tyr-Leu-Thr-Met-Lys-Ile-Arg-Asp (SEQ ID NO:8),
Ala-Tyr-Val-Thr-Met-Lys-Ile-Arg-Asp (SEQ ID NO:9),
Ala-Tyr-Met-Thr-Ile-Lys-Ile-Arg-Asp (SEQ ID NO:10),
Ala-Tyr-Met-Thr-Leu-Lys-Ile-Arg-Asp (SEQ ID NO:11),
Ala-Tyr-Met-Thr-Val-Lys-Ile-Arg-Asp (SEQ ID NO:12),
Ala-Tyr-Met-Thr-Met-Lys-Ile-Arg-Asp (SEQ ID NO:13),
Ala-Tyr-Met-Thr-Met-Lys-Met-Arg-Asp (SEQ ID NO:14),
Ala-Tyr-Met-Thr-Met-Lys-Val-Arg-Asp (SEQ ID NO:15),
Ala-Tyr-Met-Thr-Met-Lys-Ile-Arg-Gln (SEQ ID NO:16), and
Ala-Tyr-Met-Thr-Met-Lys-Ile-Arg-Glu (SEQ ID NO:17).

* * * * *

UNITED STATES PATENT AND TRADEMARK OFFICE
CERTIFICATE OF CORRECTION

PATENT NO. : 6,159,937
DATED : December 12, 2000
INVENTOR(S) : Christian Grønhøj Larsen and Borbaia Gesser It is certified that error appears in the above-identified patent and that said Letters Patent is hereby corrected as shown below:

Column 2,
Line 37, delete "BALB/C" and insert therefor -- BALB/c --.

Column 9,
Line 33, delete "IL-1γ" and insert therefor -- IL-1β --.

Column 10,
Line 3, delete "Lysile" and insert therefor -- Lys-Ile --.

Column 17,
Line 33, delete "body.".

Column 33,
Line 21, delete "Eridas" and insert therefor -- Fridas --.

Column 49,
Line 3, delete "TNFA" and insert therefor -- TNFα --.
Line 14, delete "clalm" and insert therefor -- claim --.
Line 48, delete "9" and insert therefor -- 8-10 --.

Column 50,
Line 36, delete "reperfiision" and insert therefor -- reperfusion --.
Lne 54, delete "Lye" and insert therefor -- Lys --.

Signed and Sealed this

Twenty-ninth Day of October, 2002

Attest:

JAMES E. ROGAN
Attesting Officer    Director of the United States Patent and Trademark Office

```
                           SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:1:

Ala Tyr Met Thr Met Lys Ile Arg Asn
1               5
```

(2) INFORMATION FOR SEQ ID NO:2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Ala Tyr Met Thr Ile Lys Met Arg Asn
1               5

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ala Phe Met Thr Leu Lys Leu Arg Asn
1               5

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ala Tyr Met Thr Met Lys Val Arg Glu
1               5

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Gly Tyr Met Thr Met Lys Ile Arg Asp
1               5

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Ala Phe Met Thr Met Lys Ile Arg Asp
1               5

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ala Tyr Ile Thr Met Lys Ile Arg Asp
1               5

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Ala Tyr Leu Thr Met Lys Ile Arg Asp
1               5

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Ala Tyr Val Thr Met Lys Ile Arg Asp
1               5

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Ala Tyr Met Thr Ile Lys Ile Arg Asp
1               5

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Ala Tyr Met Thr Leu Lys Ile Arg Asp
1               5

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Ala Tyr Met Thr Val Lys Ile Arg Asp
1               5

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Ala Tyr Met Thr Met Lys Ile Arg Asp
1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Ala Tyr Met Thr Met Lys Met Arg Asp
1               5

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Ala Tyr Met Thr Met Lys Val Arg Asp
1               5

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Ala Tyr Met Thr Met Lys Ile Arg Gln

```
1               5

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Ala Tyr Met Thr Met Lys Ile Arg Glu
1               5

(2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Ser Pro Gly Gln Gly Thr Gln Ser Glu
1               5

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa in position 2 is Met, Ile, Leu or
            Val; Xaa in position 4 is Met, Ile, Leu or Val;
            Xaa in position 6 is Asn, Asp, Gln or Glu.

(xi) SEQUENCE DESCRIPTION: SEQ ID NO:19:

Thr Xaa Lys Xaa Arg Xaa
1               5

(2) INFORMATION FOR SEQ ID NO:20:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa in position 1 is Met, Ile, Leu or
            Val; Xaa in position 3 is Met, Ile, Leu or Val;
            Xaa in position 5 is Met, Ile, Leu or Val;
            Xaa in position 7 is Asn, Asp, Gln or Glu.

(xi) SEQUENCE DESCRIPTION: SEQ ID NO:20:

Xaa Thr Xaa Lys Xaa Arg Xaa
1               5

(2) INFORMATION FOR SEQ ID NO:21:
```

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (D) OTHER INFORMATION: Xaa in position 1 is Tyr or Phe;
                Xaa in position 2 is Met, Ile, Leu or Val;
                Xaa in position 4 is Met, Ile, Leu or Val;
                Xaa in position 6 is Met, Ile, Leu or Val;
                Xaa in position 8 is Asn, Asp, Gln or Glu.

(xi) SEQUENCE DESCRIPTION: SEQ ID NO:21:

Xaa Xaa Thr Xaa Lys Xaa Arg Xaa
1               5

(2) INFORMATION FOR SEQ ID NO:22:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (D) OTHER INFORMATION: Xaa in position 1 is Ala or Gly;
                Xaa in position 2 is Tyr or Phe;
                Xaa in position 3 is Met, Ile, Leu or Val;
                Xaa in position 5 is Met, Ile, Leu or Val;
                Xaa in position 7 is Met, Ile, Leu or Val;
                Xaa in position 9 is Asn, Asp, Gln or Glu.

(xi) SEQUENCE DESCRIPTION: SEQ ID NO:22:

Xaa Xaa Xaa Thr Xaa Lys Xaa Arg Xaa
1               5

(2) INFORMATION FOR SEQ ID NO:23:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:23:

GCCTACATGA CAATGAAGAT ACGAAAC                                           27

(2) INFORMATION FOR SEQ ID NO:24:

(i) SEQUENCE CHARACTERISTICS:
            (A) LENGTH: 178 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:24:

Met Pro Gly Ser Ala Leu Leu Cys Cys Leu Leu Leu Leu Thr Gly Met
1               5                   10                  15

Arg Ile Ser Arg Gly Gln Tyr Ser Arg Glu Asp Asn Asn Cys Thr His
            20                  25                  30

```
Phe Pro Val Gly Gln Ser His Met Leu Leu Glu Leu Arg Thr Ala Phe
            35                  40                  45

Ser Gln Val Lys Thr Phe Phe Gln Thr Lys Asp Gln Leu Asp Asn Ile
     50                  55                  60

Leu Leu Thr Asp Ser Leu Met Gln Asp Phe Lys Gly Tyr Leu Gly Cys
 65                  70                  75                  80

Gln Ala Leu Ser Glu Met Ile Gln Phe Tyr Leu Val Glu Val Met Pro
                 85                  90                  95

Gln Ala Glu Lys His Gly Pro Glu Ile Lys Glu His Leu Asn Ser Leu
            100                 105                 110

Gly Glu Lys Leu Lys Thr Leu Arg Met Arg Leu Arg Arg Cys His Arg
            115                 120                 125

Phe Leu Pro Cys Glu Asn Lys Ser Lys Ala Val Glu Gln Val Lys Ser
        130                 135                 140

Asp Phe Asn Lys Leu Gln Asp Gln Gly Val Tyr Lys Ala Met Asn Glu
145                 150                 155                 160

Phe Asp Ile Phe Ile Asn Cys Ile Glu Ala Tyr Met Met Ile Lys Met
                165                 170                 175

Lys Ser (2) INFORMATION FOR SEQ ID NO:25:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Met His Ser Ser Ala Leu Leu Cys Cys Leu Val Leu Leu Thr Gly Val
 1               5                  10                  15

Arg Ala Ser Pro Gly Gln Gly Thr Gln Ser Glu Asn Ser Cys Thr His
             20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
     50                  55                  60

Leu Leu Lys Glu Ser Leu Leu Glu Asp Phe Lys Gly Tyr Leu Gly Cys
 65                  70                  75                  80

Gln Ala Leu Ser Glu Met Ile Gln Phe Tyr Leu Glu Glu Val Met Pro
                 85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
            115                 120                 125

Phe Leu Pro Cys Glu Asn Lys Ser Lys Ala Val Glu Gln Val Lys Asn
        130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn (2) INFORMATION FOR SEQ ID NO:26:
```

(i) SEQUENCE CHARACTERISTICS:
    (A) LENGTH: 170 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:26:

```
Met Glu Arg Arg Leu Val Val Thr Leu Gln Cys Leu Val Leu Leu Tyr
1               5                  10                  15

Leu Ala Pro Glu Cys Gly Gly Thr Asp Gln Cys Asp Asn Phe Pro Gln
                20                  25                  30

Met Leu Arg Asp Leu Arg Asp Ala Phe Ser Arg Val Lys Thr Phe Phe
            35                  40                  45

Gln Thr Lys Asp Glu Val Asp Asn Leu Leu Leu Lys Glu Ser Leu Leu
        50                  55                  60

Glu Asp Phe Lys Gly Tyr Leu Gly Cys Gln Ala Leu Ser Glu Met Ile
65                  70                  75                  80

Gln Phe Tyr Leu Glu Glu Val Met Pro Gln Ala Glu Asn Gln Asp Pro
                85                  90                  95

Glu Ala Lys Asp His Val Asn Ser Leu Gly Glu Asn Leu Lys Thr Leu
                100                 105                 110

Arg Leu Arg Leu Arg Arg Cys His Arg Phe Leu Pro Cys Glu Asn Lys
            115                 120                 125

Ser Lys Ala Val Glu Gln Ile Lys Asn Ala Phe Asn Lys Leu Gln Glu
        130                 135                 140

Lys Gly Ile Tyr Lys Ala Met Ser Glu Phe Asp Ile Phe Ile Asn Tyr
145                 150                 155                 160

Ile Glu Ala Tyr Met Thr Ile Lys Ala Arg
                165                 170
```

(2) INFORMATION FOR SEQ ID NO:27:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:27:

```
Ala Tyr Met Thr Met Lys Met Arg Lys Asn
1               5                  10
```